(12) United States Patent
Spicer et al.

(10) Patent No.: US 6,818,760 B1
(45) Date of Patent: *Nov. 16, 2004

(54) REMOVAL OF DYE-LABELED DIDEOXY TERMINATORS FROM DNA SEQUENCING REACTIONS

(75) Inventors: Douglas A. Spicer, Seattle, WA (US); Karin A. Hughes, Bothell, WA (US); Robert J. Kaiser, Bothell, WA (US); James E. Mahoney, Medina, WA (US); Amy L. Springer, Seattle, WA (US); Mark L. Stolowitz, Woodinville, WA (US); Carl H. D. Weissman, Seattle, WA (US)

(73) Assignee: Prolinx Incorporated, Bothell, WA (US)

(*) Notice: Subject to any disclaimer, the term of this patent is extended or adjusted under 35 U.S.C. 154(b) by 39 days.

This patent is subject to a terminal disclaimer.

(21) Appl. No.: 09/680,889

(22) Filed: Oct. 6, 2000

Related U.S. Application Data

(63) Continuation-in-part of application No. 09/564,117, filed on May 3, 2000, now Pat. No. 6,414,136.
(60) Provisional application No. 60/158,188, filed on Oct. 6, 1999, and provisional application No. 60/164,050, filed on Nov. 8, 1999.

(51) Int. Cl.$^7$ .................. C07H 21/02; C07H 21/04; C12Q 1/68; C12P 19/34; A61K 9/54
(52) U.S. Cl. .................. 536/25.4; 435/6; 435/91.1; 536/23.1; 536/25.3; 536/25.32
(58) Field of Search .................. 435/6, 91.1, 91.2, 435/91.5; 424/1.21, 1.25, 1.27, 458, 462; 536/23.1, 24.3, 25.32, 24.33, 25.3, 25.4

(56) References Cited

U.S. PATENT DOCUMENTS

| | | |
|---|---|---|
| 5,484,701 A | 1/1996 | Cocuzza et al. |
| 5,512,439 A | 4/1996 | Hornes et al. |
| 5,564,104 A | 10/1996 | Pourfarzaneh |
| 5,683,875 A | 11/1997 | Lichtenwalter |
| 5,790,964 A | 8/1998 | Pourfarzaneh |
| 5,827,531 A | 10/1998 | Morrison et al. |
| 5,830,912 A | 11/1998 | Gee et al. |
| 5,935,572 A | 8/1999 | Hayward et al. |
| 6,103,127 A | 8/2000 | Pourfarzaneh |

OTHER PUBLICATIONS

Ruiz–Martinez et al., "A Sample Purification Method for Rugged and High–Performance DNA Sequencing by Capillary Electrophoresis Using Replaceable Polymer Solutions. A. Development of the Cleanup Protocol," *Anal. Chem.*, 70:1516–1527 (1998).

Salas–Solano et al., A Sample Purification Method for Rugged and High–Performance DNA Sequencing by Capillary Electrophoresis Using Replaceable Polymer Solutions. B. Quantitative Determination of the Role of Sample Matrix Components on Sequencing Analysis, *Anal. Chem.*, 70:1528–1535 (1998), Sambrook et al., *Molecular Cloning: A Laboratory Manual*, Second Edition, Cold Spring Harbor Laboratory Press, p. 9.49 (1998).

BioRad Produt Catalogue, "Anonymous" Life Science Research Products, pp. 20–23 (1993).

*Primary Examiner*—Ram R. Shukla
*Assistant Examiner*—Jane Zara
(74) *Attorney, Agent, or Firm*—Townsend and Townsend and Crew LLP

(57) ABSTRACT

This invention provides methods for removing unincorporated dye-labeled molecules from a mixture that includes dye-labeled polynucleotides or other polymers and the unincorporated dye-labeled molecules. The methods involve adsorbing the unincorporated dye-labeled molecules into a plurality of particles that are made up of one or more porous hydrophobic materials that are encapsulated in a hydrophilic matrix.

50 Claims, 12 Drawing Sheets

(6 of 12 Drawing Sheet(s) Filed in Color)

ddA          ddG

REMOVAL OF DYE-LABELED DIDEOXY TERMINATORS FROM DNA SEQUENCING REACTIONS

CROSS-REFERENCE TO RELATED APPLICATIONS

This application is a continuation-in-part of U.S. application Ser. No. 09/564,117, filed May 3, 2000, now U.S. Pat. No. 6,414,136, which application claims benefit of U.S. Provisional Application Nos. 60/158,188, filed Oct. 6, 1999 and 60/164,050, filed Nov. 8, 1999. Each of these applications are incorporated herein by reference for all purposes.

BACKGROUND OF THE INVENTION

1. Field of the Invention

This invention pertains to the field of the purification of polynucleotides from mixtures that contain fluorescent dye-labeled molecules. The polynucleotides can include, for example, reaction products from nucleic acid sequencing reactions.

2. Background

The demands of the Human Genome Project and the commercial implications of polymorphism and gene discovery have driven the development of significant improvements in DNA sequencing technology. Contemporary approaches to DNA sequencing have imposed stringent demands on reliability and throughput for DNA sequencers. Recent reports have demonstrated the extraordinary potential of capillary electrophoresis (CE) for DNA sequencing given the inherent speed, resolving power and ease of automation associated with this method as compared to slab gel electrophoretic methods (Carrilho et al., *Anal. Chem.* 1996, 68, 3305–3313; Tan and Yeung,*Anal. Chem.* 1997, 69, 664–674; Swerdlow et al., *Anal. Chem.* 1997, 69, 848–855).

Relative to cross-linked gel capillary electrophoretic columns, the recent development of replaceable polymer solutions to achieve size separation of single-stranded DNA fragments has increased the lifetime of the columns and eliminated the requirements of gel pouring and casting (Ruiz-Martinez et al., *Anal. Chem.* 1993, 65, 2851–2858). Additionally, improvements in the composition of the separation matrix have led to sequencing over 1000 bases per run (Carrilho et al., *Anal. Chem.* 1996, 68, 3305–3313). Automated capillary electrophoresis systems for DNA sequencing have been introduced commercially by three major scientific instrument manufacturers (Beckman Coulter CEQ™ 2000 DNA Analysis System; Amersham Pharmacia MegaBACE 1000 DNA Sequencing System; and PE Biosystems ABI Prism 3700 DNA Analyzer).

Realizing the potential of this new generation of automated DNA sequencers is proving difficult, however, as problems in read length and accuracy remain, primarily due to the limitations associated with the methods currently available for purifying the products of cycle sequencing reactions. Indeed, the critical importance of sample preparation for the successful implementation of capillary electrophoresis has not been sufficiently emphasized.

In contrast to slab gel electrophoresis, primer extension products are introduced into the capillary column using electrokinetic injection, which provides focusing of the single-stranded DNA fragments at the head of the column (Swerdlow et al., *Proc. Natl. Acad. Sci. U.S.A.* 1988, 85, 9660–966). However, electrokinetic injection is biased toward high electrophoretic mobility ions, such as chloride, deoxynucleotides and dideoxynucleotides, which, if present in the sequencing reaction solution, negatively affect the focusing of single-stranded DNA fragments. Consequently, to increase the amount of DNA injected into the capillary column, and to improve the focusing of the injected DNA, an effective removal of these small ionic species is required.

A further group of especially problematic high electrophoretic mobility ions are the dye-labeled fluorescent dideoxynucleotide terminators, and in particular the recently commercialized terminators having two fluorescent moieties configured as energy transfer pairs (e.g., ABI PRISM Big-Dye™ Terminators from PE Biosystems and DYEnamic ET™ Terminators from Amersham Pharmacia). These reagents, and the hydrolysis products derived therefrom, have been found to be particularly difficult to remove from primer extension reactions, resulting in the presence of fluorescent artifacts (routinely described as "dye blobs") that negatively affect the automated analysis of sequencing data (Rosenblum, B.; Lee, L.; Spurgeon, S.; Khan, S.; Menchen, S.; Heiner, C. and Chen, S., *Nucleic Acids Research*, 1997, 25, 4500–4504). Dye-labeled sequencing primers, when employed as an alternative to dye-labeled terminators, afford similar problems (Jingyue, J.; Ruan, C.; Fuller, C.; Glazer, A. and Mathies, R., *Proc. Natl. Acad. Sci. USA*, 1995, 92, 4347–4351. Jingyue, J.; Kheterpal, I.; Scherer, J.; Ruan, C.; Fuller, C.; Glazer, A. and Mathies, R.,*Anal. Biochem.*, 1995, 231, 131–140. Jingyue, J.; Glazer, A. and Mathies, R., *Nucleic Acids Research*, 1996, 24, 1144–1148. Lee, L.; Spurgeon, S.; Heiner, C.; Benson, S.; Rosenblum, B.; Menchen, S.; Graham, R.; Constantinescu, A.; Upadhya, K. and Cassel, J., *Nucleic Acids Research*, 1997, 25, 2816–2822).

Fluorescent energy transfer dye-labeled dideoxynucleotide triphosphate terminators suitable for use in DNA sequencing are described in U.S. Pat. No. 5,800,996. Fluorescent energy transfer dye-labeled primers suitable for use in DNA sequencing are described in U.S. Pat. Nos. 5,688, 648, 5,707,804 and 5,728,528.

During the course of cycle-sequencing reactions, deoxynucleotide triphosphates (dNTPs) and dye-labeled dideoxynucleotide triphosphates (ddNTPs) undergo hydrolysis of the phosphate ester bonds during the denaturation step that proceeds each amplification cycle when the temperature is elevated to from 95° C. to 99° C. This results in the generation of dye-labeled artifacts including dideoxynucleotide diphosphates (ddNDPs), dideoxynucleotide monophosphates (ddNMPs) and dideoxynucleosides. The ddNTPs derived from the pyrimidine bases, dideoxythymidine (ddTTP) and dideoxycytidine (ddCTP), are particularly labile in this regard. The dye-labeled ddNTPs, ddNDPs and ddNMPs elute from capillary electrophoretic columns prior to the dye-labeled primer extension products, and consequently do not directly interfere with the interpretation of the sequencing data. However, the intensity of the signals associated with the dye-labeled ddNTPs, ddNDPs and ddNMPs may exceed those of the primer extension products by many orders of magnitude. This discontinuity in signal intensity has proven problematic with respect to automated base-calling software, resulting, in a worse-case scenario, in the software interpreting the fluorescent artifact peaks as primer extension products and the primer extension products as baseline noise. A further significant complication is associated with the presence of dye-labeled dideoxynucleosides, in that they are found to co-elute from both capillary electrophoretic columns and slab gels with the primer extension products. Not only is the intensity of the artifact signal disproportionately high as compared to the signals associated with the primer extension products, but the width of the peak is sufficiently broad to obscure the analysis of from 5 to 20 bases.

The sample preparation scheme now routinely employed for both slab gel electrophoresis and CE consists of desalting DNA sequencing samples by ethanol or isopropanol precipitation, followed by reconstitution of the DNA fragments and template in a mixture of formamide-0.5 M EDTA (49:1) prior to loading or injection (Figeys et al., 1996, 744, 325–331; Sambrook, J.; Fritsch, E. F.; Maniatis, T. *Molecular Cloning: A Laboratory Manual*; Cold Spring Harbor Laboratory Press: Cold Spring Harbor, N.Y., 1989; section 9.49). Although widely utilized, this method has been found to exhibit variable reproducibility in terms of DNA recovery, to provide marginal performance with respect to the quantitative removal of dye-labeled artifacts, and is not easily automated (Tan, H.; Yeung, E. S. *Anal. Chem.* 1997, 69, 664–674, and Hilderman, D.; Muller, D. *Biotechniques* 1997, 22, 878–879).

High electrophoretic mobility ionic species in DNA sequencing samples are not the only contaminants that cause degradation in sequencing read length. Template DNA also has been shown to interfere with the analysis of primer extension products in both thin slab gels (Tong et al., *Biotechniques* 1994, 16, 684–693), and capillary columns (Swerdlow et al., *Electrophoresis* 1996, 17, 475–483). Upon injection of the sequencing reaction solution, a current drop and significant deterioration in the resolving power of the capillary column is observed when template DNA is present in the sample (Salas-Solano et al., *Anal. Chem.* 1998, 70, 1528–1535). However, at present, template DNA removal is seldom considered an essential aspect of sample preparation for DNA sequencing by capillary electrophoresis.

Two approaches to sample preparation that address the need for removal of template and other reactants have been proposed thus far. In the first approach, which is described in U.S. Pat. No. 5,484,701, a biotinylated primer enables the capture and purification of primer extension products on streptavidin magnetic particles. After extensive washing of the primer extension products immobilized on the streptavidin magnetic particles to remove the sequencing reaction constituents including template DNA and unincorporated deoxynucleotides and dideoxynucleotides, release of the primer extension products from the particles is effected by heating the streptavidin magnetic particles to from about 90° C. to 100° C. in a formamide solution.

Although this approach has considerable utility in conjunction with slab gel electrophoresis (in which formamide is often added to sequencing samples to facilitate denaturation of duplex DNA and to increase the viscosity of the sample to facilitate slab gel loading), it has recently been shown to be problematic when utilized in conjunction with capillary electrophoresis. At least three distinct problems (exclusive of cost) have been identified as being associated with this approach. First, the formamide solution utilized to effect release of immobilized primer extension products is incompatible with electrokinetic injection, owing to the high ionic strength of the solution due to the presence of high electrophoretic mobility ions (most notably 10 mM EDTA or 30–140 mM sodium acetate in 95% formamide). In the absence of salt in the formamide solution, the efficiency of release of biotinylated primer extension products has been shown to be significantly reduced from >95% to <40% (Tong and Smith, *Anal. Chem.* 1992, 64, 2672–2677). The effective ionic strength of the release solution has been shown to be still further increased by decomposition of 95% formamide that occurs when the solution is heated and results in release of ammonia.

Second, samples recovered from streptavidin magnetic particles are found to be contaminated with protein derived from streptavidin. Release of immobilized primer extension product results from the denaturation of the streptavidin that is covalently linked to the magnetic particle. Streptavidin is a multi-subunit protein with a high isoelectric point. Denaturation of immobilized streptavidin is always accompanied by the concomitant release of those protein subunits that are not covalently linked to the magnetic particles. This contaminating protein acts in a manner somewhat analogous to template DNA, as a consequence of its anionic character and high molecular weight. Finally, dye-labeled fluorescent dideoxynucleotide terminators, and hydrolysis products derived therefrom, have been found to bind nonspecifically to streptavidin magnetic particles, and to be released into the formamide solution upon denaturation of streptavidin. Thus, the nonspecifically bound terminators can accompany the "purified" primer extension product and adversely impacting the subsequent analysis.

A second approach to purification of primer extension products that includes removal of template DNA and unincorporated reactants utilizes a multi-step methodology involving: (1) Ultrafiltration to remove template DNA; (2) Vacuum concentration to reduce sample volume; (3) Size exclusion chromatography (two sequential gel filtration columns) to reduce the ionic strength and remove dye-labeled artifacts; and (4) Vacuum concentration to reduce sample volume prior to analysis (Ruiz-Martinez et al., *Anal. Chem.* 1998, 70, 1516–1527, and Salas-Solano et al., *Anal. Chem.* 1998, 70, 1528–1535). Although this approach affords excellent samples for CE analysis, it is generally complex, costly, time consuming and unsuitable for automation in a high throughput environment. In fact, as compared to the throughput potential of multi-column capillary electrophoresis DNA sequencers, the aforementioned methodology would constitute the rate-limiting step in a sequencing laboratory.

The methods currently employed to purify primer extension products for analysis by capillary and slab gel electrophoresis have been summarized above. Although ethanol or isopropanol precipitation are known to reduce the level of both high electrophoretic mobility ions and dye-labeled artifacts present in the sample, the residual level of dye-labeled artifacts remains problematic. Size exclusion chromatography in spin columns can remove both high electrophoretic mobility ions and dye-labeled artifacts, but is the least automation compatible for high throughput environments and the most expensive. Additionally, the use of spin columns results in considerable sample dilution, often introducing the necessity for a precipitation or evaporation step to concentrate the sample prior to analysis. The biotin/streptavidin methodology should, in principle, quantitatively remove dye-labeled artifacts. However, dye-labeled artifacts bind nonspecifically to immobilized streptavidin and are released along with the primer extension products when the sample is heated in formamide. Another disadvantage of the biotin/streptavidin methods is that short molecules are preferentially adsorbed to the matrix, resulting in a decrease in signal for longer molecules.

Thus, none of the methods currently available provide for the quantitative removal of all of the potentially contaminating constituents associated with DNA sequencing reactions. Consequently, a method is needed to circumvent this considerable limitation if the extraordinary potential of capillary electrophoresis for DNA sequencing is to be realized in the not too distant future. The present invention fulfills this and other needs.

SUMMARY OF THE INVENTION

The present invention provides methods for removing fluorescent or other dye-labeled molecules from a mixture that includes one or more polymers, such as polynucleotides, into which dye-labeled molecules are incorporated as well as the unincorporated dye-labeled molecules. The methods involve contacting the mixture with a plurality of particles that are composed of a cross-linked three-dimensional hydrophilic polymeric matrix that has trapped within it a porous adsorptive hydrophobic material. The unincorporated dye-labeled molecules pass through the hydrophilic matrix and become preferentially adsorbed onto the porous hydrophobic materials. Subsequent removal of the particles from the mixture thus also removes the adsorbed dye-labeled molecules from the mixture that includes the polymers.

In some embodiments, the invention provides methods for the purification of fluorescently labeled primer extension products derived from polymerase chain reactions (PCR) and cycle sequencing reactions (CSR). The primer extension reaction mixtures generally contain unincorporated dye-labeled primers and/or terminators, including dye-labeled energy transfer primers and terminators (ddNTPs), as well as their hydrolysis products, which include dye-labeled ddNDPs, ddNMPs and dideoxynucleosides. The methods afford samples that are substantially free of fluorescent artifacts and thus are suitable for DNA sequencing by either capillary or slab gel electrophoresis.

The methods of the invention involve, in some embodiments, extending a primer by means of a template-directed primer extension reaction in the presence of either dye-labeled primers or dye-labeled terminators;

contacting the constituents of the primer extension reaction with a plurality of particles that are composed of a cross-linked three-dimensional hydrophilic polymeric matrix in which porous adsorptive hydrophobic materials are entrapped, so as to effect the preferential absorption to the particles of the dye-labeled primers or dye-labeled terminators, as well as dye-labeled artifacts derived therefrom; and physically separating the particles from the liquid phase that contains the remaining constituents of the primer extension reaction.

Some embodiments of the methods of the invention further involve purifying the liquid phase that contains the remaining constituents of the primer extension reaction, if necessary, and analyzing the liquid phase that contains the remaining constituents of the primer extension reaction by capillary or slab gel electrophoresis.

The invention also provides methods for preparing dye-labeled polynucleotides that are substantially free of unincorporated dye-labeled reactants. These methods involve:

(a) annealing a primer to a template and contacting the annealed primer with a polymerase in a reaction mixture that comprises the dye-labeled reactant, thereby extending the primer to form a plurality of dye-labeled polynucleotides;

(b) contacting the reaction mixture with a plurality of particles that are composed of porous hydrophobic materials that are retained within a hydrophilic polymeric matrix, so as to effect the preferential absorption of the unincorporated dye-labeled reactant, and dye-labeled artifacts derived therefrom; and (c) separating the particles of (b) from the reaction mixture that contains the dye-labeled polynucleotides.

Other aspects of the invention include, for example, the use of blocking reagents to precondition the magnetic particles so as to minimize the nonspecific binding of primer extension products.

BRIEF DESCRIPTION OF THE DRAWINGS

This patent contains at least one drawing executed in color. Copies of this patent with color drawing(s) will be provided by the Patent and Trademark Office upon request and payment of the necessary fee.

Careful inspection of the baseline reveals that dye-labeled ddT artifact cannot be detected. Primer extension products terminated with ddA are depicted in green; primer extension products terminated in ddT are depicted in red; primer extension products terminated in ddC are depicted in blue; and primer extension products terminated with ddG are depicted in black. The software assigns an "N" to primer extension products that can not be identified.

Figure 11:
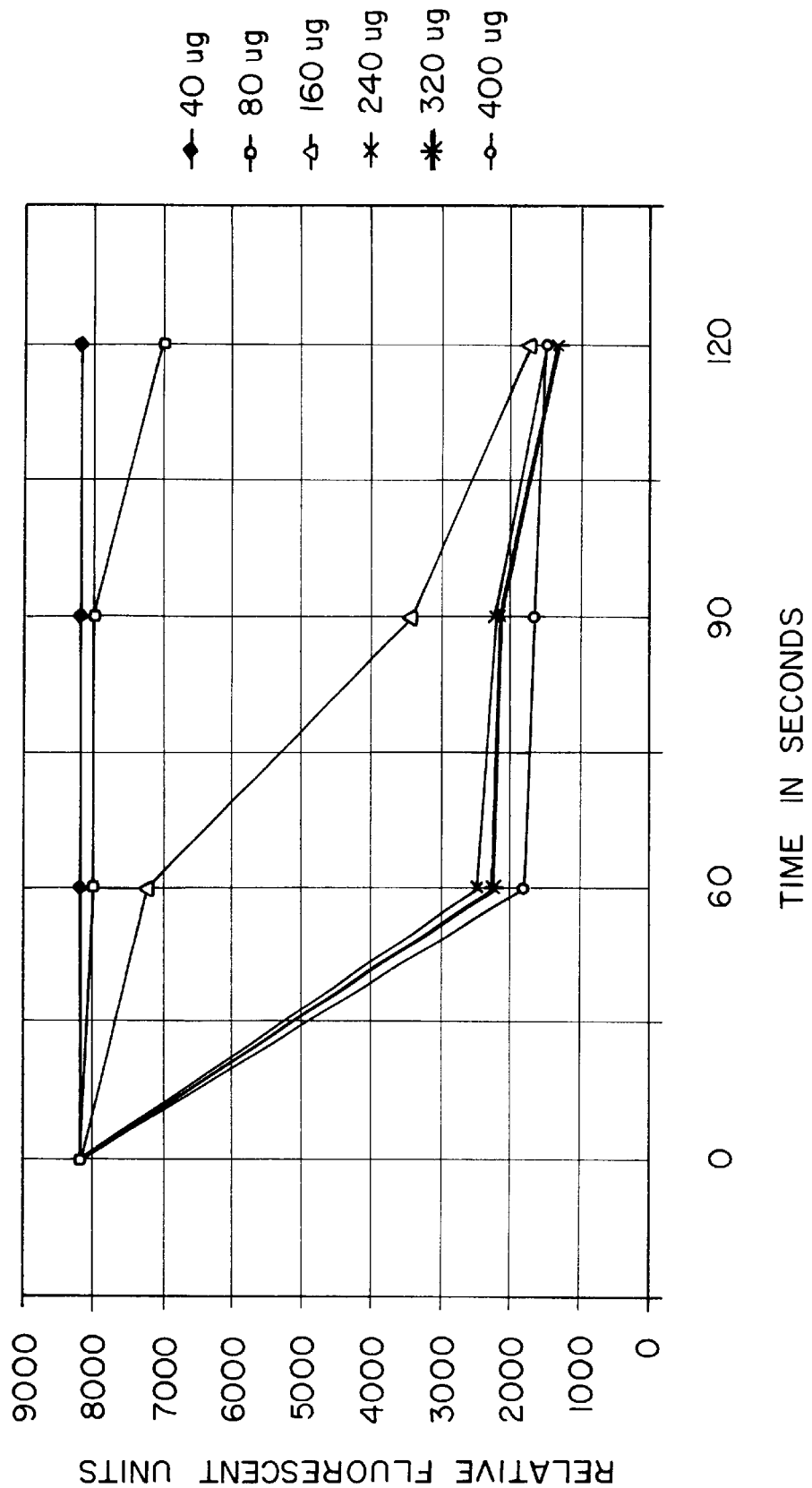

FIG. 11 shows a time course of the removal of fluorescent dNTPs by MagaCharc™ beads. The relative amount of fluorescence was determined over time between zero and 120 seconds.

Figure 12:
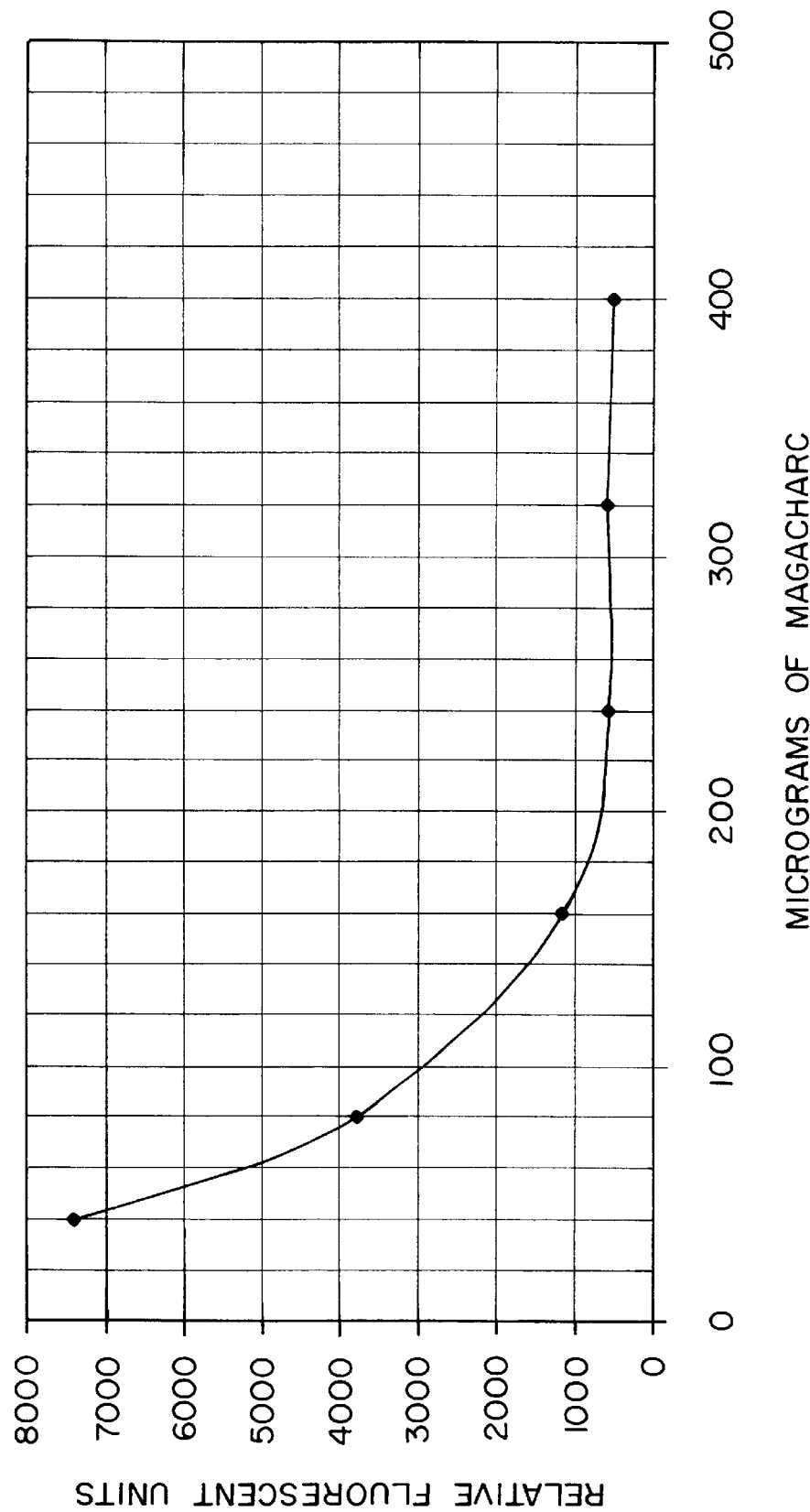

FIG. 12 shows a response curve for increasing amounts of MagaCharc™ beads added to a mixture of fluorescent dNTPs. The beads were incubated with the dNTPs for one minute and removed. Relative fluorescent units remaining were then determined.

Figure 13:
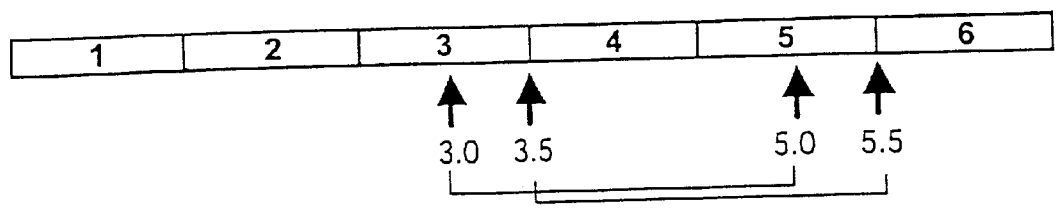

FIG. 13 shows an example of vortex calibration.

DETAILED DESCRIPTION

The present invention provides methods and kits for removing unincorporated dye-labeled molecules from a mixture that includes a plurality of dye-labeled polymer molecules (e.g., polynucleotides) and the unincorporated dye-labeled molecules. The methods of the invention provide an efficient and effective means by which one can remove unincorporated dye-labeled molecules from the products of, for example, DNA sequencing reactions. The removal of the unincorporated dye-labeled molecules from the reaction products greatly reduces or eliminates artifacts that can result from the presence of unincorporated dye-labeled molecules in samples that are loaded onto, for example, gels or capillary electrophoresis columns for analysis.

Moreover, the methods are simple to perform and highly efficient, and are amenable to high-throughput, automated sequencing. Purification of dye-labeled polynucleotides using the methods of the invention is particularly well suited to automation. One need not carry out a centrifugation step or a vacuum filtration step, both of which are difficult to adapt to an automated robotic sequencing system. Another significant advantage of the methods and kits of the invention is that the use of modified (e.g., biotinylated) primers is not required.

The methods involve contacting a mixture that contains a plurality of dye-labeled polynucleotides, as well as dye-labeled molecules that are not incorporated into the polynucleotide, with a plurality of particles that are composed of a cross-linked hydrophilic polymeric matrix in which are entrapped crystalline or particulate porous hydrophobic materials to which the dye-labeled molecules can adsorb. The unincorporated dye-labeled molecules pass rapidly through the hydrophilic matrix and become adsorbed onto the hydrophobic materials, while the dye-labeled molecules that are incorporated into polynucleotides are inhibited from passing through the hydrophilic matrix due to their molecular size. The particles are then removed from the mixture, thus also removing the adsorbed unincorporated dye-labeled molecules.

The methods of the present invention are useful for the purification of primer extension products that are substantially free of dye-labeled artifacts that result from the presence of dye-labeled ddNTPs and the hydrolysis products derived therefrom. The products are obtained in a form that is optimal for automated DNA sequencing by slab gel or particularly capillary electrophoresis, and for other analytical methods.

Primer Extension Reactions

The purification methods of the invention are useful for purifying a wide variety of products that are obtained by polymerase-mediated, template-directed extension of oligonucleotide primers. These reactions are often used in the characterization of nucleic acids, including DNA and RNA. The purification methods can be used, for example, to purify the products of polymerase chain reaction, ligase chain reaction, and other amplification methods that employ primer extension and/or ligation. These and other protocols that involve primer extension are known to those of skill in the art. Examples of these techniques are found in Berger and Kimmel, *Guide to Molecular Cloning Techniques, Methods in Enzymology* 152 Academic Press, Inc., San Diego, Calif. (Berger); Sambrook et al. (1989) *Molecular Cloning—A Laboratory Manual* (2nd ed.) Vol. 1–3, Cold Spring Harbor Laboratory, Cold Spring Harbor Press, NY, (Sambrook et al.); *Current Protocols in Molecular Biology*, F. M. Ausubel et al., eds., Current Protocols, a joint venture between Greene Publishing Associates, Inc. and John Wiley & Sons, Inc., (1994 Supplement) (Ausubel); Cashion et al., U.S. Pat. No. 5,017,478; and Carr, European Patent No. 0,246,864. Examples of techniques sufficient to direct persons of skill through in vitro amplification methods are found in Berger, Sambrook, and Ausubel, as well as Mullis et al., (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) C&EN 36–47; *The Journal Of NIH Research* (1991) 3: 81–94; (Kwoh et al. (1989) *Proc. Nat'l. Acad. Sci. USA* 86: 1173; Guatelli et al. (1990) *Proc. Nat'l. Acad. Sci. USA* 87, 1874; Lomell et al. (1989) *J. Clin. Chem.*, 35: 1826; Landegren et al., (1988) *Science*, 241: 1077–1080; Van Brunt (1990) *Biotechnology*, 8: 291–294; Wu and Wallace, (1989) *Gene*, 4: 560; and Barringer et al. (1990) *Gene*, 89:117.

The purification methods of the invention are particularly useful where a very clean primer extension product preparation is required. DNA sequencing, in particular where capillary electrophoresis is used, provides an illustrative example of an analytical method for which the methods of the invention can solve major drawbacks that have prevented capillary lectrophoresis-mediated DNA sequencing from reaching its full potential.

Figure 1:
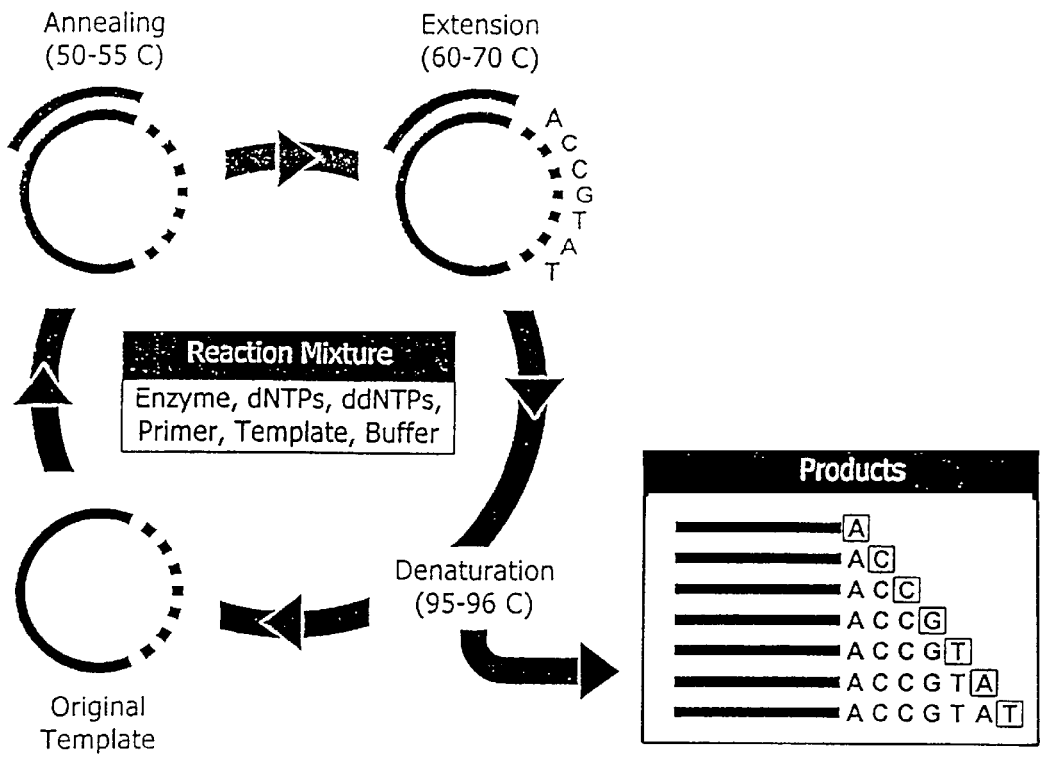
FIG. 1 summarizes the cycle sequencing methodology from which the invention can be used to purify the primer extension products. A sequencing ladder is generated by repetition of several cycles in which a primer is first annealed to template DNA that provides a hybrid suitable for subsequent extension of the primer by the action of a thermal stable DNA polymerase in the presence of deoxynucleotide triphosphates. Each of the primer extension products is eventually terminated by incorporation of a dye-labeled dideoxynucleotide triphosphate terminator.
Figure 2:
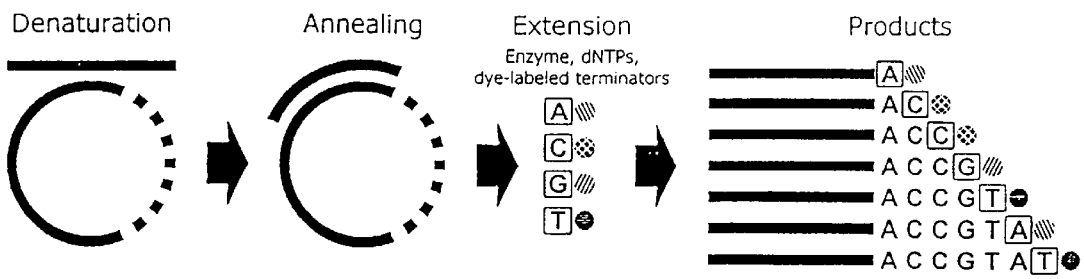
FIG. 2 illustrates the cycle sequencing methodology while emphasizing that a fluorescent dye-labeled dideoxynucleotide triphosphate terminator can be substituted for an unlabeled terminator, thereby generating a sequencing ladder suitable for detection in an automated DNA sequencer having fluorescence detection capabilities.

DNA cycle sequencing reactions are typically carried out as summarized in FIG. 1. In a typical embodiment, a primer is allowed to hybridize to the template DNA at a suitable annealing temperature, which is generally between about 50° C. and about 55° C., in preparation for primer extension. The polymerase enzyme, deoxynucleotide triphosphates (dNTPs), dideoxynucleotide terminators (ddNTPs) and other necessary reactants are added to the annealed template-primer complex, and the reaction mixture is incubated at an appropriate temperature for the particular polymerase, which is generally between about 60° C. and about 70° C. for a thermostable polymerase or between about room temperature and about 37° C. for a non-thermostable polymerase, resulting in template-directed extension of the primers. The complex that is formed between the extended primers and the template DNA is then denatured, e.g., by heating to a temperature of between about 95° C. and about 99° C., or other suitable method. This effects release of the terminated primer extension products and liberates the template DNA prior to initiating a second cycle of primer extension (FIG. 2). Routinely, this cycle is repeated from about 10 to 50 times.

Figure 3:
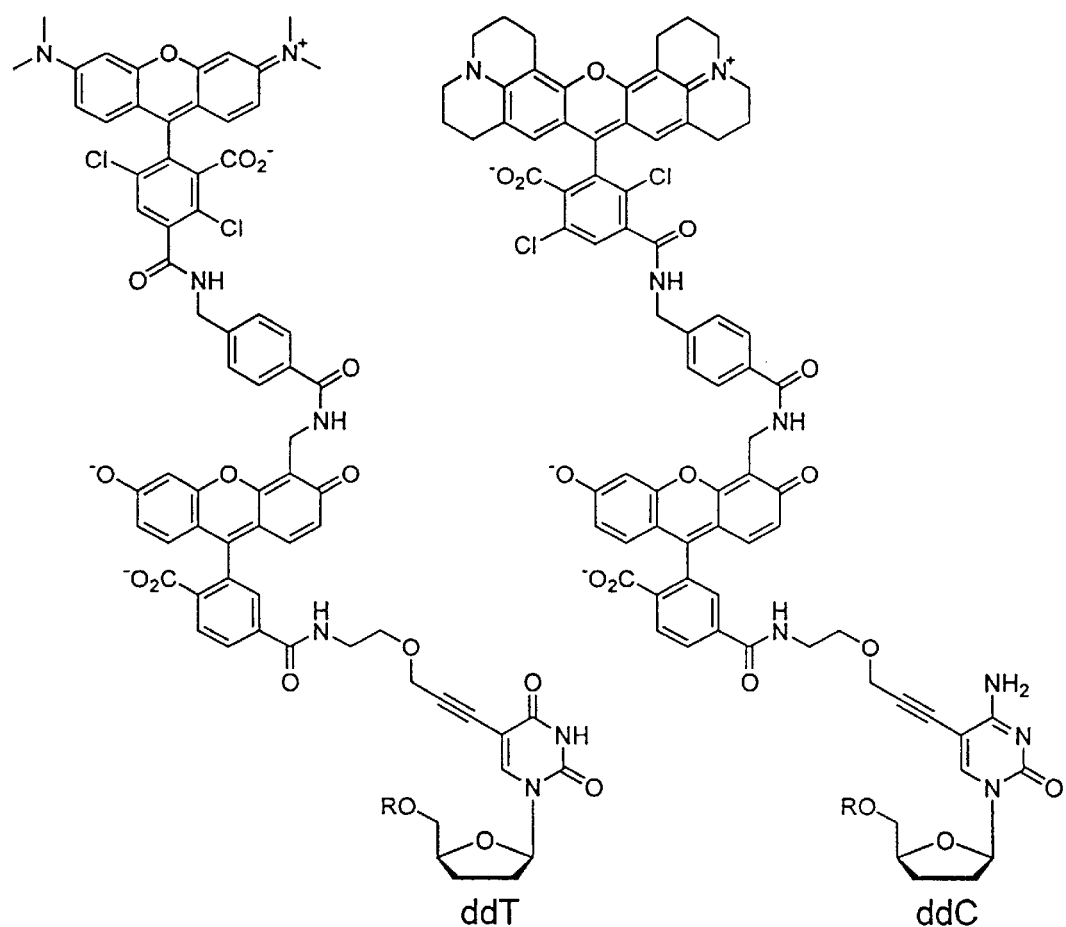
FIG. 3 illustrates the chemical structures of the dye-labeled BigDye™ Terminators (PE Applied Biosystems, Foster City Calif.) derived from the pyrimidine bases thymine and cytosine. For dideoxythymidine (ddT), R is OH; for dideoxythymidine monophosphate (ddTMP), R is $HPO_4^-$, for dideoxythymidine diphosphate (ddTDP), R is $HP_2O_7^{2-}$; and for dideoxythymidine triphosphate (ddTTP), R is $HP_3O_{10}^{3-}$. For dideoxycytidine (ddC), R is OH; for dideoxycytidine monophosphate (ddCMP), R is $HPO_4^-$, for dideoxycytidine diphosphate (ddCDP), R is $HP_2O_7^{2-}$; and for dideoxycytidine triphosphate (ddCTP), R is $HP_3O_{10}^{3-}$.
Figure 4:
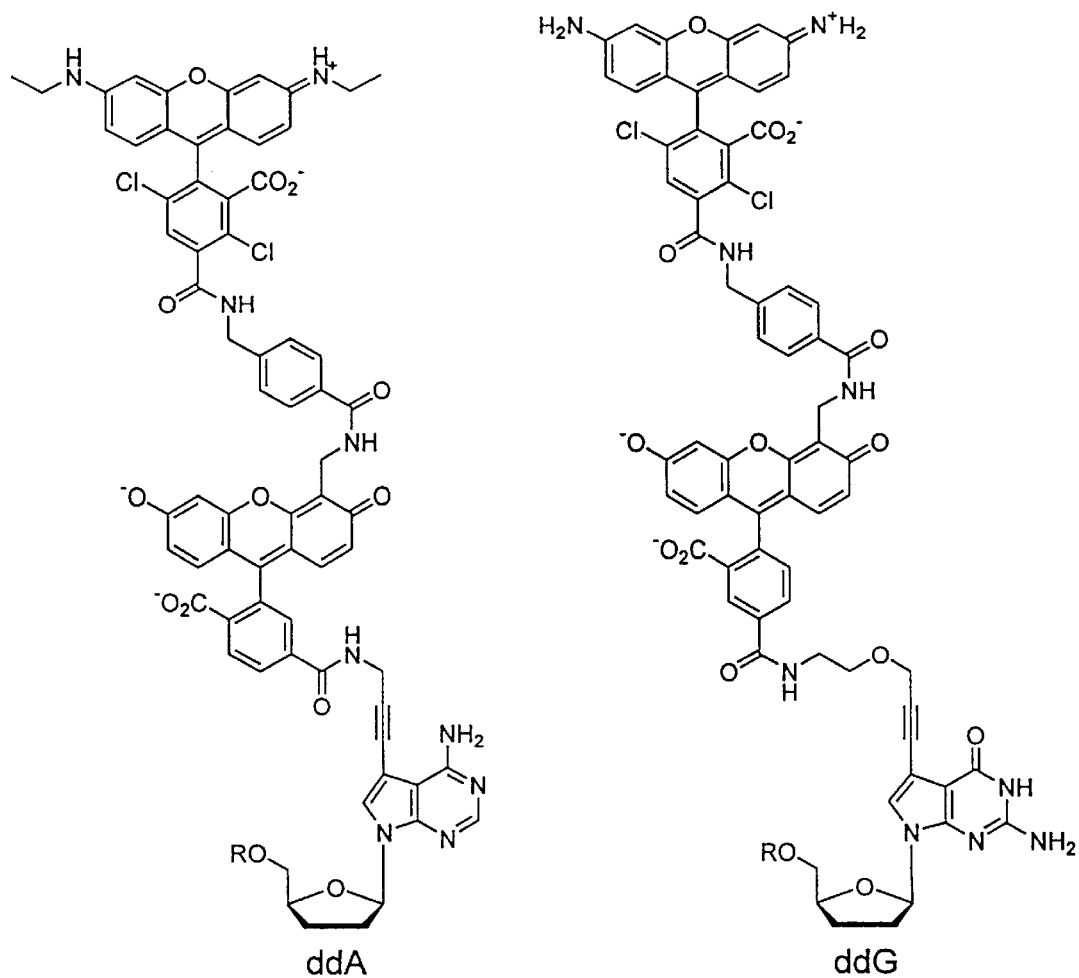
FIG. 4 illustrates the chemical structures of the dye-labeled BigDye™ Terminators (PE Applied Biosystems, Foster City Calif.) derived from the purine bases adenine and guanine. For dideoxyadenosine (ddA), R is OH; for dideoxyadenosine monophosphate (ddAMP), R is $HPO_4^-$, for dideoxyadenosine diphosphate (ddADP), R is $HP_2O_7^{2-}$; and for dideoxyadenosine triphosphate (ddATP), R is $HP_3O_{10}^{3-}$. For dideoxyguanosine (ddG), R is OH; for dideoxyguanosine monophosphate (ddGMP), R is $HPO_4^-$, for dideoxyguanosine diphosphate (ddGDP), R is $HP_2O_7^{2-}$; and for dideoxyguanosine triphosphate (ddGTP), R is $HP_3O_{10}^{3-}$.

The reaction mixtures and resulting primer extension products produced in the aforementioned cycle contain, in some embodiments, dye-labeled dideoxynucleotide terminators. The chemical structures of the dye-labeled dideoxynucleotide terminators contained within the ABI PRISM® BigDye™ Terminator Cycle Sequencing Ready Reaction Kit are shown in FIGS. 3 and 4. The dideoxynucleotide triphosphates derived from the pyrimidine bases (ddCTP and ddTTP) are illustrated in FIG. 3, and the dideoxynucleotide triphosphates derived from the purine bases (ddATP and ddGTP) are illustrated in FIG. 4. These reagents represent the state of the art and are each comprised of two dyes configured as energy transfer pairs. In each of the reagents the fluorescein moiety acts as an energy transfer donor and the rhodamine moiety as a energy transfer acceptor. The efficiency of energy transfer approaches 100%. The brightness of these reagents is 2- to 3-fold greater than the previous generation of dideoxynucleotide terminators that were derived from the dichlororhodamines. However, the BigDye™ terminators are particularly hydrophobic and exhibit limited solubility at neutral and low pH. Consequently, BigDye™ terminators, and the hydrolysis products derived therefrom, have proven particularly difficult to remove from primer extension products.

Hydrolysis of BigDye™ terminators, which results in progressive dephosphorylation of the nucleotide triphosphate, and is thought to occur during the denaturation stage of the cycle sequencing reaction when the temperature to elevated to between 95° C. to 99° C., produces the corresponding ddNDPs, ddNMPs and dideoxynucleosides. The ddNTPs initially present in the reaction are less hydrophobic than the ddNDPs which result from their hydrolysis, and the ddNDPs are less hydrophobic than the ddNMPs which result from hydrolysis of the ddNDPs. The ddNMPs in turn are less hydrophobic than the dideoxynucleosides which result from hydrolysis of the ddNMPs. The ddNTPs derived from the pyrimidine bases are more susceptible to hydrolytic dephosphorylation than the ddNTPs derived from the purine bases. The mechanistic basis for this differentiation has not been explained.

Purification of Primer Extension Products

The invention provides methods for the purification of primer extension products to eliminate or reduce the amount of unincorporated dye-labeled dideoxynucleotide triphosphates (ddNTPs), and hydrolysis products derived therefrom (ddNDPs, ddNMPs and dideoxynucleosides), that are present in the preparation of primer extension products. The methods involve contacting the primer extension reaction constituents, after thermal cycling, for a precise period of from about 10 seconds to 5 minutes, more preferably between about 10 seconds and about 2 minutes, with particles that are composed of a cross-linked hydrophilic polymeric matrix. Entrapped within the cross-linked hydrophilic matrix are porous hydrophobic materials. The reaction mixtures and particles are typically mixed by vortexing.

A. Particles

The adsorptive porous hydrophobic materials used in the methods of the invention are preferably of a composition that selectively retains from an aqueous solution of moderate to high ionic strength relatively low molecular weight organic molecules that exhibit hydrophobic properties. The hydrophobic properties of the molecules can be due to, for example, the presence of predominately aromatic and aliphatic hydrocarbon substituents such as dye molecules. The molecules can also exhibit limited solubility in aqueous solution.

The hydrophobic materials used in the particles are often (but not necessarily) crystalline or particulate, and are preferably comprised of activated charcoal, porous hydrophobic polymers, or either alkyldimethylsilane- or aryldimethylsilane-coated silica and glass particles. Examples of suitable hydrophobic polymers include divinylbenzene, latex, polystyrene and polymethylmethacrylate. Examples of suitable alkyldimethylsilane and aryldimethylsilane treated silica and glass particles include those prepared from butyldimethylchlorosilane (C4), octyldimethylchlorosilane (C8), octadecyldimethylsilane (C18) and phenyldimethylsilane. In presently preferred embodiments, the mean diameter of the porous hydrophobic materials is approximately two orders of magnitude smaller than the diameter of the particle. Particles that include a hydrophobic material are described in, for example, U.S. Pat. No. 5,790,964.

The porous hydrophobic materials are entrapped within a hydrophilic matrix, such as a cross-linked, three-dimensional hydrophilic polymeric matrix. This matrix is relatively highly permeable to low and relatively low molecular weight molecules (i.e., those having a molecular weight of less than about 5,000 daltons) such as unincorporated fluorescently-labeled deoxynucleotides and dideoxynucleotides, so such molecules can pass through the matrix while larger molecules (e.g., primer extension products) cannot. The degree of porosity and permeability of the hydrophilic matrix can be varied by changing the percentage of cross-linking associated with the matrix. Matrices can be prepared from, for example, acrylamide, agarose or dextran, by cross-linking with appropriate reagents so as to entrap the porous hydrophobic materials while simultaneously controlling the porosity of the hydrophilic matrix. In presently preferred embodiments, the hydrophilic matrices are polyacrylamide, cross-linked at between about 2.5–15%, and most preferably have about 5% cross-linking. The particles are usually three-dimensional, of an irregular shape, and typically have mean diameters of from about 5 to 40 microns.

In a preferred embodiment, the particles also include a magnetizable constituent to allow the particles to be separated from a mixture by placing the particles in proximity to a magnet. A variety of different magnetizable constituents are suitable for use in the particles. These include, for example, ferric oxide, nickel oxide, barium ferrite, and ferrous oxide. Suitable magnetic particles can be prepared by, for example, mixing equivalent amounts of iron oxide and hydrophobic particles (e.g., charcoal) with acrylamide/bis-acrylamide. These components are vigorously mixed to form a "cake," which is then passed through a coffee grinder or equivalent. The ground material is then passed through a ball mill to obtain particles that are preferably about 5–20 $\mu$m in diameter.

MagaCharc™ AA particles (Cortex Biochem, San Leandro Calif.) are an example of a commercially available particle that is suitable for use in the methods of the invention. MagaCharc™ particles are prepared by cross-linking of a 1:1 mixture (w/w) of charcoal (Norit SX-Ultra) and iron oxide ($Fe_3O_4$) within a polymeric matrix that is prepared from 80% (w/w) polyacrylamide cross-linked with 5% N,N-methylene-bis-acrylamide and containing 15% (w/w) acrylic acid. The presence of the iron oxide distributed throughout the particle, preferably uniformly, renders the particle magnetizable and thereby facilitates the removal of supernatants from the particles by placing the particles in proximity to a magnet.

Nonspecific absorption associated with a hydrophilic matrix can be reduced by including an acrylic acid or methacrylic acid monomer during the polymerization of the matrix. This ensures that the matrix exhibits a residual anionic charge which is mutually repulsive, from an electrostatic standpoint, with respect to the polynucleotides that are present in the primer extension reaction.

Another way to reduce nonspecific binding is to precondition the particles with one of several reagents known to minimize the nonspecific absorption of nucleic acids on blotting membranes including bovine serum albumin (BSA), Denhardt's reagent, heparin sulfate, linear polyacrylamide (LPA), nonfat dried milk, polyvinylpyrrolidone (PVP), salmon sperm DNA and Tween 20. For example, particles are preferably batch preconditioned with heparin sulfate.

B. Purification Methods

To effect removal of the unincorporated dye-labeled deoxynucleotides or dideoxynucleotides from the desired primer extension products, the particles are added to the mixture that contains the primer extension products and the unincorporated dye-labeled deoxynucleotides or dideoxynucleotides (e.g., a primer extension reaction or cycle sequencing reaction). The hydrophobic unincorporated ddNTPs, ddNDPs, ddNMP and dideoxynucleosides selectively permeate the hydrophilic coating of the particles, owing to their relatively low molecular weight as compared to the primer extension products, and are absorbed by the hydrophobic cores. After an appropriate incubation period, which generally also involves mixing, the particles are removed from the mixture. The unincorporated dye molecules are removed along with the particles, thus leaving the desired labeled polynucleotides substantially free of the dye molecules.

Relatively short primer extension products can also be absorbed into the particles. However, the loss of short primer extension products can be rendered unimportant by the judicious choice of an appropriate primer. In general terms, the efficiency of dye-labeled terminator removal has been found to be related to the hydrophobicity of each reagent. Consequently, ddNMPs are more efficiently removed than ddNDPs, which are more efficiently removed than ddNTPs.

The purification methods of the invention are conveniently carried out in microtiter plates. The use of microtiter plates facilitates automation of the purification process using robotic systems. Ninety-six well microtiter plates are often used, and for very small reaction volumes (e.g., ~15 $\mu$l), 192 or 384 well plates can be used. The use of small reaction volumes reduces the cost per reaction by reducing the amount of reagents required.

The particles can be added to the reaction mixtures as an aqueous suspension. Alternatively, a suspension of particles in a liquid can be placed in a microtiter plate well or other container to be used for the purification procedure and the liquid phase can be removed prior to adding the reaction mixtures to the particles. For example, a suspension of magnetic particles can be placed in a well of a microtiter plate, which is then placed in the presence of a magnetic field to collect the particles. The liquid is then removed from the well before adding the reaction mixture to the well.

The reaction mixtures and the particle suspensions should be allowed to come to room temperature before adding the particles to the reaction mixtures. For samples that have been stored at 4° C., this usually takes approximately 15 minutes.

It is often desirable to optimize the purification conditions for a particular dye-labeled reactant, amount of dye-labeled reagent in each reaction, reaction volume, dilution buffer, and/or particular sequencing instrument. For example, DNA sequencers such as the Applied Biosystems Prism 3700®

DNA Analyzer, which use laminar flow heads, are more sensitive to purification than are other sequencers. Similarly, the use of different dilutions of commercially available DNA sequencing kit reagents can affect the optimal conditions for purification.

Purification method variables that can be adjusted to optimize the purification obtained include the amount of particles used per reaction, the time of incubation and mixing, and intensity of mixing. Relatively quick optimization of the purification conditions can be achieved by setting up reactions in a microtiter plate. Conveniently, two of the three variables are fixed, while the third is varied to determine the optimum purification condition for a particular combination of reagents and sequencer. For example, varying amounts of particles can be added to different wells of the microtiter plate, and the incubation time and intensity of mixing held constant to determine an optimal amount of particles. Alternatively, the wells can each have the same amount of particles and the mixing intensity held constant, while the time of incubation is varied to determine the optimum incubation time. Similarly, to obtain the optimum mixing intensity, one can vary the mixing intensity while the amount of particles and the incubation time are held constant. After removal of the particles from the reaction mixtures, the samples are then run on a sequencer, and the conditions that provide the best results are then employed routinely for that sequencer and dye reagent. Generally, it is quite convenient to use a constant amount of particles in each well and vary the incubation time and/or mixing intensity to obtain optimum conditions for a particular situation.

The amount of particles used in the methods is that amount which is sufficient to remove substantially all of the unincorporated dye-labeled molecules. Generally, between about 1 $\mu$g and 10 $\mu$g (inclusive) of particles is added per 1 $\mu$l of reaction mixture. More preferably, between 3 $\mu$g and 7 $\mu$g (inclusive) of particles is added per 1 $\mu$l of reaction mixture, and still more preferably the amount of particles added is between 4 $\mu$g and 6 $\mu$g per $\mu$l of reaction mixture. For example, about 100 $\mu$g to about 1 mg, more preferably about 200 $\mu$g to about 600 $\mu$g of particles, and still more preferably about 300 $\mu$g to about 400 $\mu$g of particles are typically added to about 100 $\mu$l of reaction mixture. The amount of dye-labeled molecules in the reaction mixture is a significant factor in determining the particle amount. Therefore, for a smaller reaction volume that has a similar amount of dye-labeled molecule than a larger reaction volume, the amount of particles per $\mu$l of reaction mixture can be proportionately greater than for the larger volume. For example, each well of a 384 well microtiter plate used to purify a reaction volume of only 15 $\mu$l can nevertheless contain 100 $\mu$g to about 1 mg, more preferably about 200 $\mu$g to about 600 $\mu$g of particles, and still more preferably about 300 $\mu$g to about 400 $\mu$g of particles.

The particles are incubated in the reaction mixture for a precise period of time, generally between about ten seconds to about 5 minutes. More preferably, the incubation time is about 30 seconds to about 2 minutes. During the incubation, it is preferable to mix the reaction mixtures thoroughly. As described above, the incubation time and mixing intensity are variables that can be optimized to achieve the best results.

Mixing can be by any method known to those of skill in the art, including pipetting up and down, and the like. This mixing method is particularly suitable for use with a robotic system, thus allowing one to completely automate the purification process. Vortexing is another particularly suitable method for mixing. One example of a suitable commercially available vortexer is the Vortex Genie 2 Model G-560 (Fisher, Pittsburgh, Pa., Catalog No. 12-812). For use with microtiter plates, the Vortex Genie 2 96-well plate head is suitable (Fisher, Catalog No. 12-812C).

When using a vortexer, it is desirable to calibrate the vortexer prior to use. The optimal setting for a vortexer is determined by extrapolation from the "splash threshold" (the speed setting at which 100 $\mu$l of liquid begins to splash out of a well). Two full steps are subtracted from the splash threshold to obtain the optimal setting for use in the methods of the invention. For example, if splashing starts at a setting of 5.0, the calibrated setting for use in the purification methods is 3.0 (FIG. 13). When performing the calibration, it is preferred to use a polypropylene plate because polystyrene plates have a greater surface tension and a higher splash threshold than polypropylene plates. If a polystyrene plate is nevertheless used for the calibration, the calibrated setting is the splash threshold −3.5. The calibration is preferably performed by adding 100 $\mu$l of an aqueous liquid (e.g., colored water) to two or three wells of a microtiter plate. The plate is placed on a vortex microtiter plate head with the vortex speed set at zero. The vortexer is turned on and the speed is slowly increased. Vortexing is stopped periodically to check for splashing outside the wells. The liquid will appear to be vortexing fairly vigorously before splashing is observed.

After incubation of the samples with the particles, the particles are removed from the reaction mixtures. Removal can be by any suitable method known to one of skill in the art (e.g., filtration). In preferred embodiments, magnetic particles are employed and removal is accomplished by placing the sample containers in contact with a magnet. Suitable magnets include, for example, neodynium magnets that exhibit greater than 12 KGs (Kgauss) reminance. Magnets that have rare earth magnetic elements such as the Prolinx RapXtract™ Magnetic Separator are suitable.

The supernatant can be removed for use after separation of the particles. For example, the samples can be placed on a loading plate which contains loading buffer for use in a sequencer.

The purification methods of the invention substantially remove the unincorporated dye-labeled reactants from the primer extension products. By "substantially remove" is meant that at least about 60% of the unincorporated dye-labeled reactants are removed from a mixture. More preferably, at least about 75% of the unincorporated dye-labeled reactants are removed, still more preferably at least about 90%, and most preferentially substantially all of the unincorporated dye-labeled reactants are removed.

C. Purification Kits

The invention also provides kits for carrying out the purification methods of the invention. For example, the invention provides kits that include one or more microtiter plates which have aliquots of the particles in some or all of their wells. Such kits allow ready incorporation of the purification methods of the invention into an automated sequencing operation. The kits can also include written instructions for the use of the particles to remove unincorporated dye-labeled reactants from polynucleotides. For example, the instructions can provide information as to optimal mixing conditions, incubation times, and the like.

In some embodiments, the wells of the microtiter plates contain an amount of the particles that has been determined to provide optimal results for a given dye-labeled reactant, for a given dilution of the reactant, and/or for a particular DNA sequencer. For example, the invention provides kits in which the microtiter plate wells contain an amount of particles that is optimized for a PE Biosystems ABI PRISM® 373, 377, 310, or 3700 sequencer using a specific dilution of PE Biosystems BigDye® Ready Reaction Mix. For example, one kit would be optimized for use with a PRISM® 373 using a 4:20 (total µl BigDye® Ready Reaction Mix: total µl reaction volume) dilution. Table 1 shows the amounts of particles per well in kits for the indicated specific sequencers and dilutions of BigDye® Ready Reaction Mix.

TABLE 1

| Instrument | Dilution* | Amount of Particles (µg) per Well |
|---|---|---|
| PRISM ® 373 | 4:20 | 600 |
| PRISM ® 373 | 2:20 | 600 |
| PRISM ® 373 | 4:10 | 600 |
| PRISM ® 373 | 2:10 | 400 |
| PRISM ® 377 | 4:20 | 600 |
| PRISM ® 377 | 2:20 | 600 |
| PRISM ® 377 | 4:10 | 600 |
| PRISM ® 377 | 2:10 | 400 |
| PRISM ® 310 | 4:20 | 600 |
| PRISM ® 310 | 2:20 | 600 |
| PRISM ® 310 | 4:10 | 600 |
| PRISM ® 310 | 2:10 | 400 |
| MJGeneSys BaseStation | 2:20 | 600 |

*Total µl BigDye ® Ready Reaction Mix:total µl reaction volume

In other embodiments, the wells of the microtiter plate contain a constant amount of particles. Optimization of such plates for a particular reaction mixture dilution and/or sequencing apparatus involves varying the time and/or intensity of vortexing, rather than varying the amount of particles. For example, the invention provides microtiter plates in which one or more wells contain between about 100 µg and 1 mg of the particles. More preferably, the wells contain between about 200 and 800 µg, and still more preferably between about 300 and 600 µg of particles in one or more wells. Each well that contains particles contains approximately the same amount of particles. To optimize these microtiter plates for a particular template, dilution, sequencing apparatus, and the like, one can test different incubation/mixing times, and/or different mixing intensities. The microtiter plates of the invention, in some embodiments, contain a constant amount of particles in each well of the microtiter plate.

The microtiter plates included in the kits can have a film seal that allows one to use only a portion of the wells at a time, preserving the remaining wells for future use. This provides for economical use of all wells and reduces waste.

EXAMPLES

The following examples are offered to illustrate, but not to limit the present invention.

Example 1

Purification of Primer Extension Products from the ABI PRISM® BigDye™ Terminator Cycle Sequencing Ready Reaction Kit by Isopropanol Precipitation A region of pUC19 plasmid DNA was sequenced by DNA Cycle Sequencing using modifications to the ABI PRISM® BigDye™ Terminator Cycle Sequencing Ready Reaction Kit (PE Applied Biosystems, Foster City Calif.). For each sample, the following ingredients were dispensed into MicroAmp™ Reaction tubes with caps (PE Applied Biosystems): 2 µL of pUC19 template DNA (125 ng/µL), 4 µL of primer (1 pmol/µL, M13/pUC-48 24mer), 6 µL of HPLC grade water, and 8 µL of Terminator Ready Reaction Mix (PE Applied Biosystems). Capped tubes were placed in a GeneAmp PCR System 9700 Thermal Cycler (PE Applied Biosystems) preheated to 96° C. The reactions were denatured at 96° C. for five minutes and extended by 30 thermal cycles at 96° C. for 20 seconds, 50° C. for 20 seconds and 60° C. for 4 min.

Figure 5:
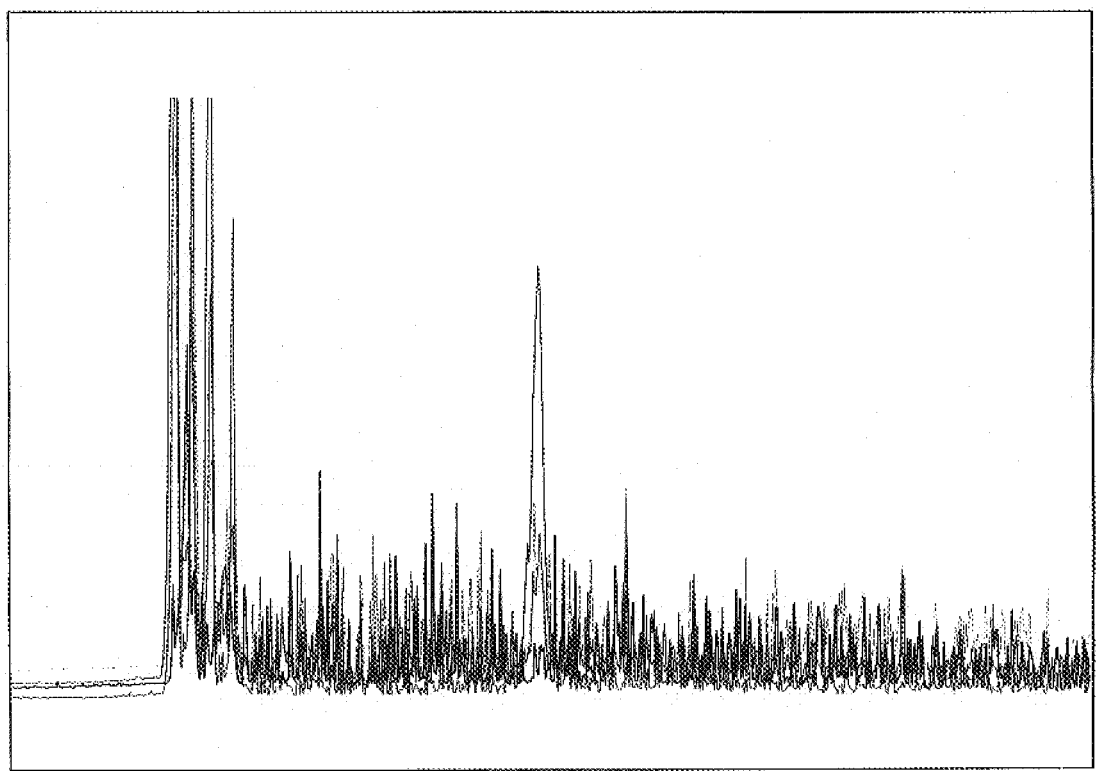
FIG. 5 illustrates the raw data recorded on an Perkin Elmer ABI PRISM™ 310 Genetic Analyzer. The primer extension products were purified by isopropanol precipitation as recommended by the instrument manufacturer. Note the presence of dye-labeled artifacts in the front on the capillary electrophoretic separation (ddNTPs, ddNDPs and ddNMPs) as well as the ddT artifact near the center of the electrophoretic separation. Primer extension products terminated with ddA are depicted in green; primer extension products terminated in ddT are depicted in red; primer extension products terminated in ddC are depicted in blue; and primer extension products terminated with ddG are depicted in black.
Figure 6:
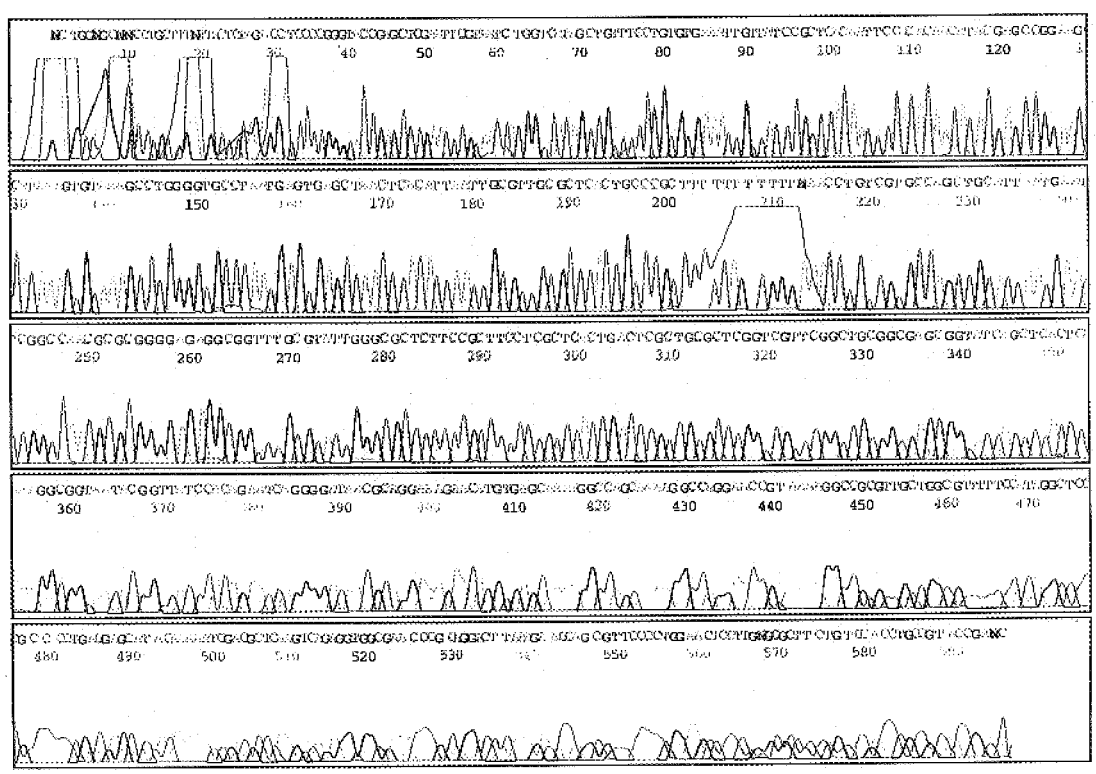
FIG. 6 shows the processed DNA sequencing data (SEQ ID NO:3) that corresponds to the raw data shown in FIG. 5. Note that the region between 200 and 214 bases has been assigned by the software the sequence GCTTT TTTTT TTTNA (SEQ ID NO:1), despite the fact that visual inspection of the processed data clearly indicates that the sequence is probably GCTTT CCAGT CGGAA (SEQ ID NO:2). This anomaly results from the presence of the dye-labeled ddT artifact in the capillary electrophoretic separation. Primer extension products terminated with ddA are depicted in green; primer extension products terminated in ddT are depicted in red; primer extension products terminated in ddC are depicted in blue; and primer extension products terminated with ddG are depicted in black. The software assigns an "N" to primer extension products that cannot be identified.

After thermal cycling, the reactions were purified away from dye-labeled terminators and other reaction constituents by isopropanol precipitation. Twenty µL of deionized water and 60 µL of isopropanol was added to each of the Micro-Amp™ tubes (60% isopropanol in final volume). The tubes were sealed and the contents mixed by inverting several times. Allowed tubes to stand at room temperature for 15 min. Collected precipitate by centrifugation at 2000×g for 45 min. Discarded supernatant and centrifuged at 700×g for 1 min. Dissolved precipitate in 20 µL of formamide containing 10% (w/v) sorbitol and analyzed sample on an ABI PRISM™ 310 Genetic Analyzer (PE Applied Biosystems) by capillary electrophoresis. The raw data recorded is illustrated in FIG. 5. Note the presence of dye-labeled artifacts in the front on the capillary electrophoretic separation (ddNTPs, ddNDPs and ddNMPs) as well as the ddT artifact near the center of the electrophoretic separation. The processed DNA sequencing data corresponding to the raw data is illustrated in FIG. 6. Note that the region between 200 and 214 bases has been assigned by the analysis software the DNA sequence GCTTT TTTTT TTTNA (SEQ ID NO:1), despite the fact that visual inspection of the processed data clearly indicates that the DNA sequence is probably GCTTT CCAGT CGGAA (SEQ ID NO:2). This anomaly results from the presence of the dye-labeled ddT artifact in the capillary electrophoretic separation.

Example 2

Purification of Primer Extension Products from the ABI PRISM® BigDye™ Terminator Cycle Sequencing Ready Reaction Kit by Magnetic Particle Absorption A region of pUC19 plasmid DNA was sequenced by DNA Cycle Sequencing using modifications to the ABI PRISM® BigDye™ Terminator Cycle Sequencing Ready Reaction Kit (PE Applied Biosystems, Foster City Calif.). For each sample, the following ingredients were dispensed into MicroAmp™ Reaction tubes with caps (PE Applied Biosystems): 2 µL of pUC19 template DNA (125 ng/µL), 4 µL of primer (1 pmol/µL, M13/pUC-48 24mer), 6 µL of HPLC grade water, and 8 µL of Terminator Ready Reaction Mix (PE Applied Biosystems). Capped tubes were placed in a GeneAmp PCR System 9700 Thermal Cycler (PE Applied Biosystems), preheated to 96° C. The reactions were denatured at 96° C. for five minutes and extended by 30 thermal cycles at 96° C. for 20 seconds, 50° C. for 20 seconds and 60° C. for 4 min.

After thermal cycling, the reactions were purified away from dye-labeled terminators by magnetic particle absorption. MagaCharc™ particles (Cortex Biochem, San Leandro Calif.) were batch preconditioned to minimize nonspecific absorption of primer extension products. The supernatant was removed from 5 mL of a 10% (v/v) suspension of MagaCharc™ particles and replaced with 10×Denhardt's reagent (Denhardt, D. T., *Biochem. Biophys. Res. Commun.* 1966, 23, 641). The suspension was placed on a rotary mixer for 1 hour at room temperature and then washed 3 times with 5 mL aliquots of HPLC grade water and then finally suspended in 5 mL of HPLC grade water.

To each well of a multiwell plate was added 100 µL of a 10% (v/v) suspension of MagaCharc™ particles. The multiwell plate was placed on a magnet to pellet the particles and the supernatant removed. To each well was then added 20 µL of cycle sequencing reaction product and the contents of each well were mixed by drawing the particle suspension into a pipette tip and then displacing the suspension 10 times. The multiwell plate was then placed on a magnet to pellet the particles and the supernatants transferred to sequencer sample tubes. To each of the tubes was added 20 µL of formamide containing 10% (w/v) sorbitol. The samples were mixed by vortexing briefly and analyzed on an ABI PRISM™ 310 Genetic Analyzer (PE Applied Biosystems) by capillary electrophoresis.

Figure 7:
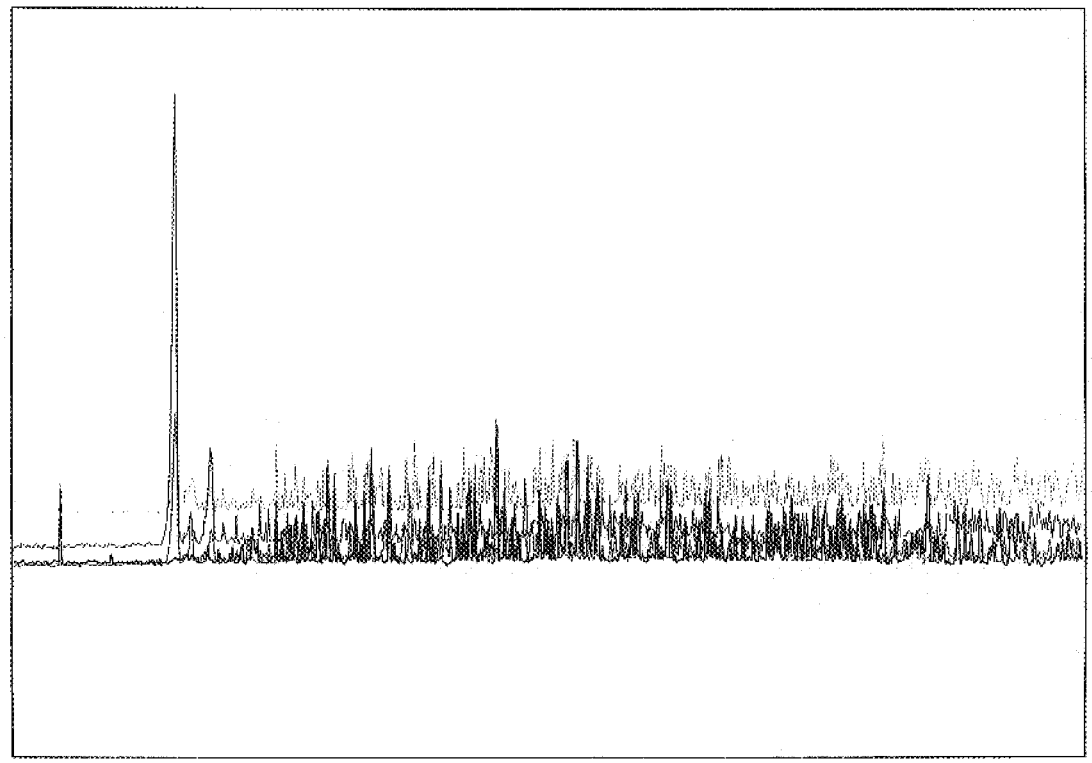
FIG. 7 illustrates the raw data recorded on an Perkin Elmer ABI PRISM™ 310 Genetic Analyzer. The primer extension products were purified by the method described herein by adding 20 μL of product to the magnetic particles pelleted from 100 μL of a 10% (v/v) suspension. The contents of each well were mixed by drawing the suspension into a pipette tip and then displacing the suspension 10 times. To each of the supernatants removed from the magnetic particles was added 20 μL of formamide containing 10% (w/v) sorbitol. The resulting solution was mixed briefly by vortexing and then analyzed. Note that after purification by the method described herein, only the ddTTP and ddTCP artifacts are recorded at magnitudes exceeding those of the primer extension products. Primer extension products terminated with ddA are depicted in green; primer extension products terminated in ddT are depicted in red; primer extension products terminated in ddC are depicted in blue; and primer extension products terminated with ddG are depicted in black.
Figure 8:
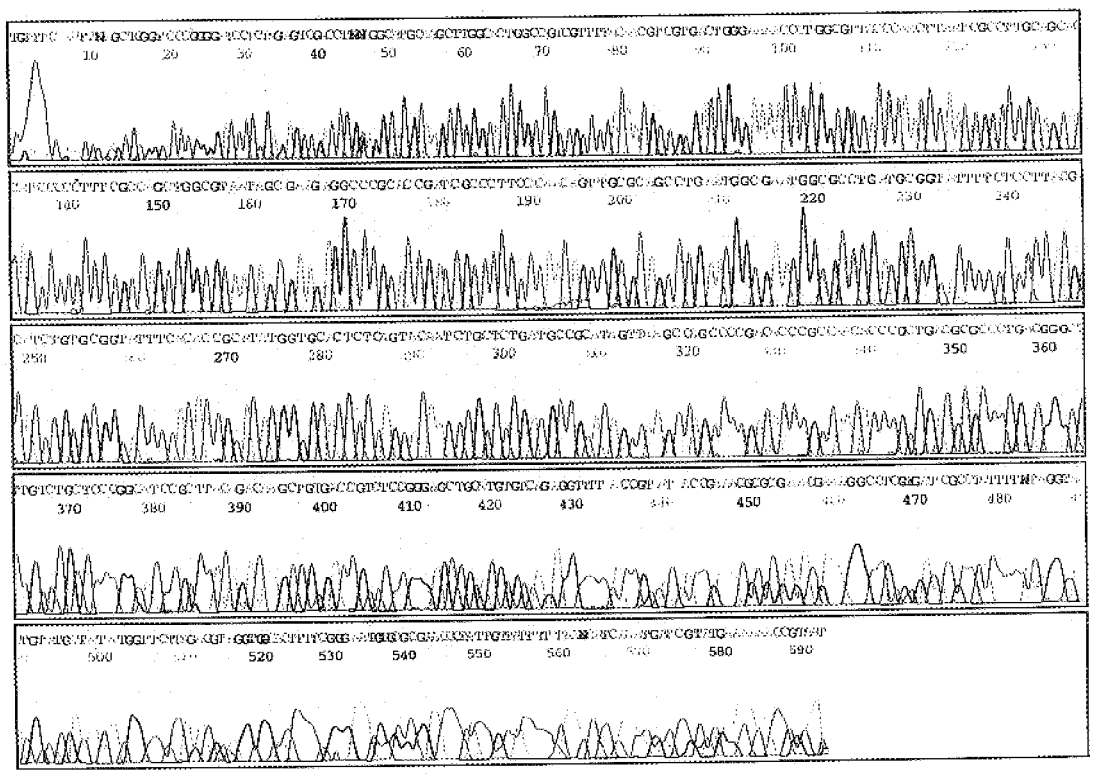
FIG. 8 shows the processed DNA sequencing data (SEQ ID NO:4) that corresponds to the raw data shown in FIG. 7. Although some residual ddT artifact can been seen by careful inspection of the baseline in the region between 190 and 200 bases, the magnitude of the artifact signal is some low relative to the signals associated with the primer extension products that the analysis software was unimpeded. Primer extension products terminated with ddA are depicted in green; primer extension products terminated in ddT are depicted in red; primer extension products terminated in ddC are depicted in blue; and primer extension products terminated with ddG are depicted in black. The software assigns an "N" to primer extension products that can not be identified.

The raw data recorded is illustrated in FIG. 7. Note that after purification by the method described above, only the ddTTP and ddTCP artifacts are recorded at magnitudes exceeding those of the primer extension products. The processed DNA sequencing data corresponding to the raw data is illustrated in FIG. 8. Although some residual ddT artifact can been seen by careful inspection of the baseline in the region between 190 and 200 bases, the magnitude of the artifact signal is so low relative to the signals associated with the primer extension products that the analysis software assigned the correct DNA sequence even in the presence of trace amounts of the artifact.

Example 3

Purification of Primer Extension Products from ½ Reactions by Magnetic Particle Absorption A region of pUC19 plasmid DNA was sequenced by DNA Cycle Sequencing using modifications to the ABI PRISM® BigDye™ Terminator Cycle Sequencing Ready Reaction Kit (PE Applied Biosystems, Foster City Calif.). For each sample, the following ingredients were dispensed into MicroAmp™ Reaction tubes with caps (PE Applied Biosystems): 2 µL of pUC19 template DNA (125 ng/µL); 4 µL of primer (1 pmol/µL, M13/pUC-48 24mer); 6 µL of HPLC grade water; and 8 µL of Terminator Ready Reaction Mix (PE Applied Biosystems) that had been diluted (1:1) with halfBD™ Dye Terminator Sequencing Reagent (Genpak Ltd., Stony Brook N.Y.). Capped tubes were placed in a GeneAmp PCR System 9700 Thermal Cycler (PE Applied Biosystems), preheated to 96° C. The reactions were denatured at 96° C. for five minutes and extended by 30 thermal cycles at 96° C. for 20 seconds, 50° C. for 20 seconds and 60° C. for 4 min.

After the thermal cycling, the reactions were purified away from dye-labeled terminators by magnetic particle absorption. MagaCharc™ particles (Cortex Biochem, San Leandro Calif.) were batch preconditioned to minimize nonspecific absorption of primer extension products as described in Example 2. To each well of a multiwell plate was added 100 µL of a 10% suspension of MagaCharc™ particles. The multiwell plate was placed on a magnet to pellet the particles and the supernatant removed. To each well was then added 20 µL of cycle sequencing reaction product and the contents of each well were mixed by drawing the particle suspension into a pipette tip and then displacing the suspension 10 times. The multiwell plate was then again placed on a magnet to pellet the particles and the supernatants transferred to sequencer sample tubes.

Figure 9:
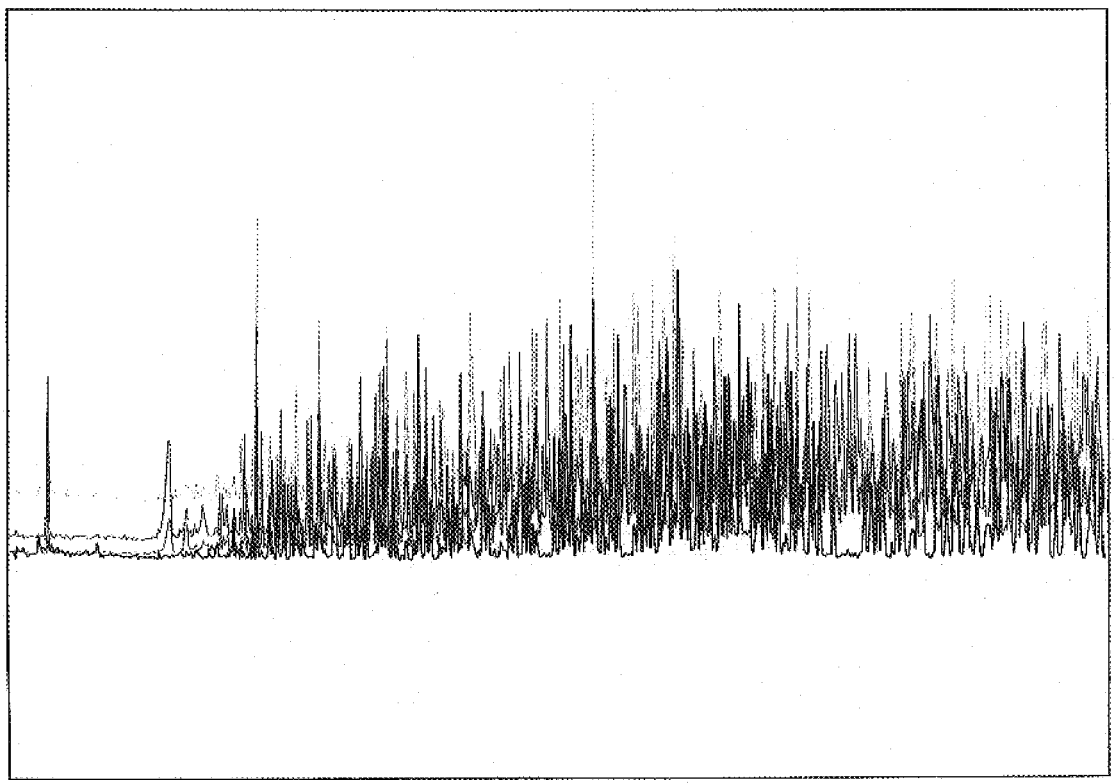
FIG. 9 illustrates the raw data recorded on an Perkin Elmer ABI PRISM™ 310 Genetic Analyzer. The primer extension products were generated from a cycle sequencing reaction comprised of 2 μL of pUC19 template DNA (125 ng/μL), 4 μL of primer (M13/pUC primer-48 24mer), 6 μL of HPLC grade water, and 8 μL of Terminator Ready Reaction Mix (PE Applied Biosystems) diluted 1:1 with halfBD™ Dye Terminator Sequencing Reagent (Genpak, Ltd., Stony Brook N.Y.). The primer extension products (20 μL) were added to the magnetic particles retained from 100 μL of a 10% (w/v) suspension in each well of a multiwell plate. The contents of each well were mixed by drawing the suspension into a pipette tip and then displacing the suspension 10 times. The multiwell plate was placed on a magnet to pellet the particles and the supernatants transferred to sequencer sample tubes. To each of the tubes was added 20 μL of formamide containing 10% (w/v) sorbitol. The samples were mixed by vortexing briefly and analyzed. Note that after purification by the method described above, none of the dye-labeled artifacts were recorded at magnitudes exceeding those of the primer extension products. Primer extension products terminated with ddA are depicted in green; primer extension products terminated in ddT are depicted in red; primer extension products terminated in ddC are depicted in blue; and primer extension products terminated with ddG are depicted in black.
Figure 10:
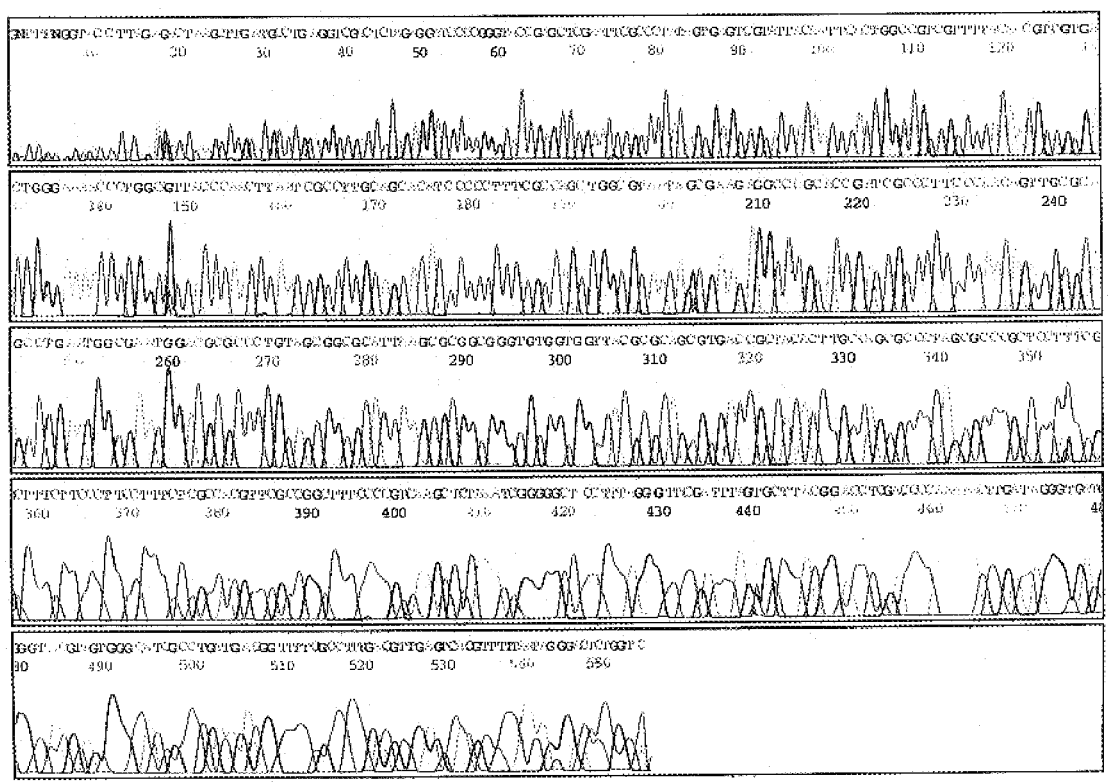
FIG. 10 shows the processed DNA sequencing data (SEQ ID NO:5) that corresponds to the raw data shown in FIG. 9.

To each of the tubes was added 20 µL of formamide containing 10% (w/v) sorbitol. The samples were mixed by vortexing briefly and analyzed on an ABI PRISM™ 310 Genetic Analyzer (PE Applied Biosystems) by capillary electrophoresis. The raw data recorded is illustrated in FIG. 9. Note that after purification by the method described above, none of the dye-labeled artifacts are recorded at magnitudes exceeding those of the primer extension products. The processed DNA sequencing data corresponding to the raw data is illustrated in FIG. 10. Careful inspection of the baseline reveals that dye-labeled ddT artifact cannot be detected.

Example 4

Time Course and Titration Curve for Removal of Fluorescent Dye-labeled Deoxynucleotides This Example shows a time course and a titration curve for the removal of unincorporated fluorescent dye-labeled deoxynucleotides using MagaCharc™ particles (Cortex Biochem, San Leandro Calif.). 8 µl of Big Dye in a total volume of 20 µl (mock reaction containing no template) was heated to 96° C. for 30 min.

The time course experiment was conducted by adding the amounts of MagaCharc™ particles shown in FIG. 11 to the mixture of dye-labeled deoxynucleotides. The samples were mixed by vortexing and incubated for the indicated time periods. The relative fluorescent units remaining in the mixture for each of the time points is shown in FIG. 11. These results show that over 70% of the fluorescently labeled molecules are removed after a 60 second incubation when 240 µg or more of the magnetic particles are used. Further incubation time did not significantly increase the amount removed.

To investigate the effect of increasing amounts of magnetic particles on removal of the fluorescent dyes, mixtures of dye-labeled deoxynucleotides were heated as described above, brought to room temperature, and the indicated amounts of MagaCharc™ particles were added. The samples were vortexed for 1 minute, and the magnetic particles removed. The amount of relative fluorescent units remaining in the liquid phase was then determined.

The results of this experiment are shown in FIG. 12. The maximum effectiveness was achieved at about 200 µg of MagaCharc™ particles.

Example 5

Preparation of Sequencing Reactions

This Example describes examples of reaction conditions that are suitable for use with the purification methods and kits of the invention. In the following reaction mixtures, all template and primer DNA is preferably resuspended in deionized water. These reaction conditions are well-suited for use of pUC and pGem templates.

4:20 Reactions (4 µl BigDye® Ready Reaction Mix (PE Biosystems) in 20 µl Reaction)

Add reagents in the following order:

| | | |
|---|---|---|
| Template (125 ng/µl) | (250 ng) | 2 µl |
| Primer (1 pmole/µl) | (4 pmole) | 4 µl |
| Water | | 8 µl |
| PE Biosystems 5× Sequencing Buffer | | 2 µl |
| PE Biosystems BigDye ® | | 4 µl |
| Ready Reaction Mix | | |
| Total volume | | 20 µl |

Gently tap tube to mix
Briefly centrifuge to collect sample at the bottom of the tube For best results, prepare sequencing reactions first by preparing a master mix of BigDye® Ready Reaction Mix with PE Biosystems 5×Sequencing Buffer (e.g., a mix containing 200 μl of PE Biosystems 5×Sequencing Buffer, 400 μl of BigDye® Ready Reaction Mix and 800 μl of deionized water will be sufficient for 96 samples); and next by aliquoting 14 μl of master mix to tubes containing each primer/template mixture.

4:10 Reactions (4 μl BigDye® Ready Reaction Mix (PE Biosystems) in 10 μl Reaction)

Add reagents in the following order:

| | |
|---|---|
| Template (125 ng/μl) | 2 μl |
| Primer (1 pmole/μl) | 4 μl |
| PE Biosystems BigDye ® Ready Reaction Mix | 4 μl |
| Total volume | 10 μl |

Gently tap to mix

Briefly centrifuge to collect sample at the bottom of the tube

Example 6

Protocol for Removal of Unincorporated Dye-labeled Terminators

This Example describes protocols for removing dye-labeled terminators from DNA cycle sequencing reactions.

I. Sample Preparation

Prepare sequencing reactions according to standard protocols. As always, use high quality template DNA and template preparation kits for reliable results and take into consideration the template purity and type.

Prepare sequencing reactions according to the DNA sequencer manufacturer's recommendations. If you are using an Applied Biosystems or MJ Research instrument, examples of standard protocols follow. All template and primer DNA should be resuspended in distilled, deionized water (ddH$_2$O).

II. Example of a Typical Sequencing Reaction Protocol:

1. Prepare sequencing reactions in 96-well PCR plate.

Table 2 shows reaction mixture components for different dilutions of dye-labeled dideoxy terminator.

TABLE 2

| | Dye Dilution | | | | |
|---|---|---|---|---|---|
| | 2:10 | 4:10 | 2:20 | 4:20 | 2:20 (MJ) |
| Plasmid 250 ng, in ddH$_2$O @ 125 ng/μL | 2 μL | 2 μL | 2 μL | 2 μL | 1 μL |
| Primer 4–10 pmol in ddH$_2$O @ 1 pmol/μL | 4 μL | 4 μL | 4 μL | 4 μL | 10 μL |
| BigDye Ready Reaction Mix | 2 μL | 4 μL | 2 μL | 4 μL | 2 μL |
| BigDye 5× Diluent | 1 μL | — | 3 μL | 2 μL | NA |
| 5× Dilution Buffer (MJ) 400 mM Tris, 10 mM MgCl2, pH 9.0 | NA | NA | NA | NA | 1.2 μL |
| ddH$_2$O | 1 μL | — | 9 μL | 8 μL | qs 20 μL |

2 Gently tap tube to mix.

3 Briefly centrifuge to collect the sample at bottom of the tube.

III. Example of Typical Thermal Cycling Protocols Using Commercially Available RapExtract Kit Typical reaction conditions are shown in Table 3. Note: Use a high quality thermal cycler, such as Applied Biosystems, Eppendorf Scientific, or MJ Research.

TABLE 3

| | Typical Reaction | | MJ Basestation | |
|---|---|---|---|---|
| | Temperature (° C.) | Time (sec) | Temperature (° C.) | Time (sec) |
| Initial Denature 30+ cycles | 96 | 300 | 96 | 30 |
| Denature | 96 | 20 | 92 | 10 |
| Anneal | 50 | 20 | 55 | 5 |
| Extension | 60 | 240 | 60 | 240 |
| Hold | 4 | ∞ | 4 | ∞ |

IV. Preferred Materials and Conditions

1. Equipment

Prolinx® RapXtract Magnetic Separator, catalog #RAP1000-1

Vortex Genie 2 Model G-560

Vortex Genie 2 96-well plate head

Single- or 8-channel pipettors (one each, 200 μL and 20 μL)

2. Store at 4° C.

Store refrigerated until use. Do not freeze.

3. Use at Room Temperature

Bring to room temperature before use (approximately 15 minutes).

4. Calibrate the Vortex

Simple—but important—to do because every vortex is different. Also, check vortex calibration at least monthly or if it has been used for other applications. Vortex speeds tend to slow with age.

Speed of rotation varies from vortex to vortex. The optimal setting is determined by extrapolation from the splash threshold (the speed setting at which 100 μL of liquid begins to splash out of a well minus two full steps). For example, if splashing starts at a setting of 5.0, your calibrated setting to use for RapXtract kit is 3.0; if splashing starts at a setting of 5.5, the setting you use for RapXtract is 3.5 ("splash minus 2"). See FIG. 13.

Vortex Calibration Protocol

1 Use a polypropylene plate (polystyrene plates have greater surface tension and a higher splash threshold, however, see step 6 if you have to use a polystyrene plate).

2 Add 100 μL of aqueous liquid (such as colored water) to two or three wells.

3 Place the plate on the vortex 96-well plate head.

4 Set the speed to 0 and turn on the vortex.

5 Slowly increase the speed of the vortex and stop it periodically to check for splashing outside of the wells. Note: The liquid will appear to be vortexing fairly vigorously before you see splashing.

6 Once splashing begins, note the setting and back up the dial 2 whole numbers on the vortex—for polypropylene plates—(set at "splash minus 2"). Record this setting for future reference.

Note: Optimal mixing occurs if the setting is 2 steps below the splash threshold for polypropylene plates, or 3.5 steps below the splash threshold for polystyrene plates.

V. The Protocol

Getting Started

Allow sequencing reactions and RapXtract plates to equilibrate at room temperature for 15 minutes.

Prepare and label tubes or plates for sequencing reactions, if not already done.

Set your vortex to the proper calibration setting (splash minus 2) for use with RapXtract (see section 3, Important Requirements for Successful Use, for instructions on vortex calibration).

Procedure

1. Gently tap the RapXtract 96-well microplate on a bench top to settle the magnetic particles into the bottom of the wells.

Tip: If particles are adhering to the top film, hold the plate in your hand and gently swing your arm down and back several times. A slight flicking action may help. It is OK if a few beads are left on the film.

2. Place the RapXtract 96-well microplate on the Prolinx RapXtract Magnetic Separator with the magnetic elements (metal bars) facing up. Tap lightly to sediment the beads.

3. Using a razor blade, cut and remove the film seal to expose only the wells you want to use.

Note: When you have fewer than 96 samples, you can save the plate for later use if you leave the film intact on the unused wells and store at 4° C.

4. Set your multichannel pipette to 100 $\mu$L. Once the particles are completely settled, remove and discard the storage buffer. Take care not to remove particles (a few are OK).

Tip: The Magnetic Separator pulls particles to the same side in each column of eight wells. For easy removal of supernatant from particles, use an eight-channel pipettor and work through vertical columns of eight. The magnet and plate can be picked up and tilted, if necessary.

5. Immediately add the sequencing reactions to each well of the RapXtract plate.

6. Remove the plate from the Magnetic Separator and place the RapXtract plate on the Vortex Genie 2 equipped with the Vortex Genie 2 96-well plate head.

7. Set the vortex to your calibrated setting and vortex for the number of seconds specified in Table 4 below for the sequencing reaction dilution you use:

TABLE 4

| Dilution* ($\mu$L dye:total vol.) | Vortex time (seconds) | Dilution ($\mu$L dye:total vol.) | Vortex time (seconds) |
|---|---|---|---|
| 8:20 | 90 | 4:10 | 40 |
| 4:20 | 40 | 3:10 | 40 |
| 3:20 | 40 | 2:10 | 20 |
| 2:20 | 40 | 1:10 | 20 |
| 4:15 | 40 | 2:5 | 40 |
| 315 | 40 | 1:5 | 30 |
| 2:15 | 30 | | |
| 1:15 | 30 | | |

*All other dilutions: choose the next higher vol. and time.

NOTE:

For MJ Basestation ONLY—After vortexing, add 45 $\mu$L loading dye (100% formamide with 1 ng/$\mu$L crystal violet).

8. Place the RapXtract plate back on the RapXtract Magnetic Separator to sediment the particles.

9. Once the particles have completely settled, transfer the supernatant containing the purified reactions to the loading plate or sample tubes for loading on your sequencer.

10. Loading samples on your instrument:

Notes:

If drying down samples, note that drying time will be about 30 minutes on high heat or 60 minutes on medium heat. When samples are dry, they may appear shiny (that is, they are not wet but may appear that way).

When loading polyacrylamide gels, some particles may be carried over into the wells of the comb during loading; this does not interfere with electrophoresis.

Loading Recommendations for Specific Instruments

In general, prepare samples for loading gels or inject the samples according to your sequencer manufacturer's instructions (depending on the particular instrument you are using, e.g., evaporate samples to dryness using heat or vacuum; or electro-kinetically inject the samples). Recommendations are as shown in Table 5:

TABLE 5

| Gel-based Instruments (373 and 377) | Capillary-based systems (310 and 3700) | MJ GeneSys BaseStation |
|---|---|---|
| 1. Evaporate samples to dryness for the usual length of time (they will look shiny even when dry). 2. Thoroughly resuspend reactions in a gel loading buffer containing 80–95% deionized formamide and a suitable tracking dye (such as 2 $\mu$L). 3. Heat samples 2–3 minutes at 90–95° C. to denature. 4. Load half of the resuspended volume of each sample (such as 1 $\mu$L). Note: We recommend loading gels with a membrane comb from The Gel Company; part no. CAM 64 (www.gelcompany.com). | 310: Do not add template suppression reagent. 1. Add ddH$_2$O to bring sample volume to 30 $\mu$L, cap and vortex the tubes to mix. Tap to remove bubbles before injecting. 2. Inject the samples for 40 s at 3.5 kV (also works with the 96-well tray, micro-amp tubes and septa). 3700: Do not dry samples. Do not add formamide. Do not add template suppression reagent. 1. Add 10 $\mu$L of ddH$_2$O to the reactions. 2. Cover the sample plate with a foil seal and vortex briefly to mix. 3. Spin the plate to collect the sample at the bottom of the well. 4. Apply to the instrument using the following injection parameters: POP5-2.0 kV for 45 seconds POP6-2.5 kV for 45 seconds | Do not dry samples. Load 1 $\mu$L sample onto instrument. |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. A method for removing unincorporated dye-labeled molecules from a mixture or a reaction mixture that comprises the unicorporated dye-labeled molecules and polymers into which dye-labeled molecules are incorporated, the method comprising:

(a) contacting the mixture with a plurality of particles that comprise a porous hydrophobic material entrapped within a hydrophilic matrix;

(b) mixing and incubating the mixture and the particles for a sufficient time for dye-labeled molecules that are not incorporated into the polymer to pass into the hydrophilic matrix and become adsorbed onto the hydrophobic material; and (c) removing the particles from the mixture, thus also removing said unincorporated dye-labeled molecules adsorbed onto said hydrophobic material.

2. The method of claim 1, wherein said unicorporated and incorporated dye-labeled molecules are fluorescent dye-labeled molecules.

3. The method of claim 2, wherein the unincorporated dye-labeled molecules comprise two fluorescent dye molecules configured as an energy transfer pair.

4. The method of claim 1, wherein between 1 $\mu$g and 10 $\mu$g of particles are added per $\mu$l of mixture (a).

5. The method of claim 4, wherein between 3 $\mu$g and 7 $\mu$g of particles are added per $\mu$l of mixture (a).

6. The method of claim 5, wherein between 4 µg and 6 µg of particles are added per µl of mixture (a).

7. The method of claim 1, wherein said mixture (a) is added to between 100 µg to 1 mg of particles.

8. The method of claim 7, wherein said mixture is added to between 200 µg to 600 µg of particles.

9. The method of claim 8, wherein said mixture is added to between about 300 µg to 400 µg of particles.

10. The method of claim 1, wherein the particles are placed in a well of a microtiter plate as an aqueous suspension, the particles are collected, and the aqueous phase is removed from the well prior to adding the reaction mixture to the well.

11. The method of claim 1, wherein the polymers are polynucleotide molecules and the dye-labeled molecules are dye-labeled dideoxynucleotides.

12. The method of claim 11, wherein the mixture (a) is a reaction mixture for a primer extension reaction.

13. The method of claim 12, wherein the unincorporated dye-labeled molecules are fluorescent dye-labeled primers.

14. The method of claim 12, wherein the unincorporated dye-labeled molecules are fluorescent dye-labeled dideoxynucleotides or deoxynucleotides, or hydrolysis products thereof.

15. The method of claim 12, wherein the primer extension reaction is a DNA sequencing reaction.

16. The method of claim 15, wherein the DNA sequencing reaction is a cycle sequencing reaction.

17. The method of claim 12, wherein the primer extension reaction is a polymerase chain reaction or a ligase chain reaction.

18. The method of claim 1, wherein the particles further comprise a paramagnetic moiety.

19. The method of claim 18, wherein the paramagnetic moiety is iron oxide.

20. The method of claim 1, wherein the hydrophobic material is selected from the group consisting of activated charcoal, a hydrophobic polymer, alkyldimethylsilane- or aryldimethylsilane-coated silica and glass particles.

21. The method of claim 20, wherein the hydrophobic material comprises a hydrophobic polymer selected from the group consisting of divinylbenzene, latex, polystyrene and polymethylmethacrylate.

22. The method of claim 1, wherein the hydrophilic matrix is a cross-linked polymer selected from the group consisting of acrylamide, agarose and dextran.

23. The method of claim 1, wherein the hydrophilic matrix comprises acrylic acid or methacrylic acid.

24. The method of claim 1, wherein the particles are treated with a blocking reagent prior to contacting the mixture to reduce non-specific binding of the polymer to the particle.

25. The method of claim 24, wherein the blocking reagent is selected from the group consisting of bovine serum albumin (BSA), Denhardt's reagent, linear polyacrylamide (LPA), nonfat dried milk, polyvinylpyrrolidone (PVP), heparin sulfate, salmon sperm DNA and Tween 20.

26. A method of preparing dye-labeled polynucleotides that are substantially free of unincorporated dye-labeled reactant, the method comprising:
(a) annealing a primer to a template and contacting the annealed primer with a polymerase in a reaction mixture that comprises dye-labeled reactant, thereby extending the primer to form a plurality of dye-labeled polynucleotides;
(b) contacting the reaction mixture with a plurality of particles, wherein said particles have hydrophobic materials that are entrapped within a porous hydrophilic matrix, so as to effect the selective absorption of unincorporated dye-labeled reactant, and unincorporated dye-labeled artifacts derived therefrom; and
(c) separating the particles of (b) from the reaction mixture that contains the dye-labeled polynucleotides.

27. The method of claim 26, wherein the method further comprises:
(d) analyzing the dye-labeled polynucleotides by capillary or slab gel electrophoresis.

28. The method of claim 26, wherein the method further comprises further purifying the dye-labeled polynucleotides after separating the particles from the reaction mixture (c).

29. The method of claim 26, wherein the dye-labeled reactant is selected from dye-labeled primers and dye-labeled terminators.

30. The method of claim 29, wherein the dye-labeled reactant comprises one or more fluorescent dye-labeled dideoxynucleotides or hydrolysis products thereof.

31. The method of claim 26, wherein the particles are magnetic particles and the particles are separated from the reaction mixture (c) by placing the magnetic particles in close proximity to a magnet.

32. The method of claim 26, wherein the dye-labeled polynucleotides are products of a DNA sequencing reaction.

33. The method of claim 32, wherein the DNA sequencing reaction is a cycle sequencing reaction.

34. The method of claim 26, wherein between 1 µg and 10 µg of particles are added per µl of reaction mixture (b).

35. The method of claim 34, wherein between 3 µg and 7 µg of particles are added per µl of reaction mixture (b).

36. The method of claim 35, wherein between 4 µg and 6 µg of particles are added per µl of reaction mixture (b).

37. The method of claim 26, wherein between 100 µg and 1 mg of particles are added to the reaction mixture (b).

38. The method of claim 37, wherein between 200 µg and 600 µg of particles are added to the reaction mixture (b).

39. The method of claim 38, wherein between 300 µg and 400 µg of particles are added to the reaction mixture (b).

40. The method of claim 26, wherein the dye-labeled polynucleotides are denatured from the template prior to adding the particles.

41. A kit for removing unincorporated dye-labeled molecules from a mixture which comprises dye-labeled molecules and a polymer into which dye-labeled molecules are incorporated, wherein the kit comprises a microtiter plate having a plurality of wells, wherein one or more of the wells contain particles that comprise a hydrophilic matrix within which is incorporated a porous hydrophobic material.

42. The kit of claim 41, wherein the kit further comprises written instructions as to how to use the kit to remove unincorporated dye-labeled molecules from a mixture which comprises dye-labeled molecules and a polymer into which dye-labeled molecules are incorporated.

43. The kit of claim 41, wherein the wells that contain the particles contain between 100 µg and 1 mg of the particles.

44. The kit of claim 43, wherein the wells that contain the particles contain between 300 µg and 800 µg of the particles.

45. The kit of claim 44, wherein the wells that contain the particles contain between 400 µg and 600 µg of the particles.

46. The kit of claim 41, wherein the microtiter plate comprises a removable film seal that covers one or more of the wells that contain the particles.

47. The kit of claim 41, wherein the microtiter plate is a 96-well microtiter plate.

48. The kit of claim 41, wherein the microtiter plate is a 192-well microtiter plate.

49. The kit of claim 41, wherein the microtiter plate is a 384-well microtiter plate.

50. The kit of claim 41, wherein each well of the microtiter plate contains the particles.

* * * * *

SEQUENCE LISTING

<160> NUMBER OF SEQ ID NOS: 5

<210> SEQ ID NO 1
<211> LENGTH: 15
<212> TYPE: DNA
<213> ORGANISM: Artificial Sequence
<220> FEATURE:
<223> OTHER INFORMATION: Description of Artificial Sequence:software
      assigned sequence for region between 200 and 214
      bases
<220> FEATURE:
<221> NAME/KEY: modified_base
<222> LOCATION: (14)
<223> OTHER INFORMATION: n = g, a, c or t

<400> SEQUENCE: 1
gctttttttt tttna                                                      15

<210> SEQ ID NO 2
<211> LENGTH: 15
<212> TYPE: DNA
<213> ORGANISM: Artificial Sequence
<220> FEATURE:
<223> OTHER INFORMATION: Description of Artificial Sequence:sequence of
      region between 200 and 214 bases by visual
      inspection of processed data

<400> SEQUENCE: 2
gctttccagt cggaa                                                      15

<210> SEQ ID NO 3
<211> LENGTH: 596
<212> TYPE: DNA
<213> ORGANISM: Artificial Sequence
<220> FEATURE:
<223> OTHER INFORMATION: Description of Artificial Sequence:processed
      DNA sequencing data
<220> FEATURE:
<221> NAME/KEY: modified_base
<222> LOCATION: (1)..(596)
<223> OTHER INFORMATION: n = g, a, c or t

<400> SEQUENCE: 3
nctggngcnn cctgctttnt tactctagac ctccccgggt accgagctcg aattcgtaat      60
ctggtcatag ctgtttcctg tgtgaaattg ttatccgctc acaattccac acaacatacg     120
agccggaagc ataaagtgta aagcctgggg tgcctaatga gtgagctaac tcacattaat     180
tgcgttgcgc tcactgcccg ctttttttttt ttnaacctgt cgtgccagct gcattaatga    240
atcggccaac gcgcggggag aggcggtttg cgtattgggc gctcttccgc ttcctcgctc     300
actgactcgc tgcgctcggt cgttcggctg cggcgagcgg tatcagctca ctcaaaggcg     360
gtaatacggt tatccacaga atcaggggat aacgcaggaa agaacatgtg agcaaaaggc     420
cagcaaaagg ccaggaaccg taaaaggccg cgttgctggc gtttttccat aggctccgcc     480
cctgacgagc atacaaaaat cgacgctcaa gtcagaggtg cgaacccgc aggacttaaa     540 gaaccagcgt tcccctggaa ctccttgngc gcttctgtcc acctgccgta ccganc        596

<210> SEQ ID NO 4
<211> LENGTH: 593
<212> TYPE: DNA
<213> ORGANISM: Artificial Sequence
<220> FEATURE:
<223> OTHER INFORMATION: Description of Artificial Sequence:processed
      DNA sequencing data

```
<220> FEATURE:
<221> NAME/KEY: modified_base
<222> LOCATION: (1)..(593)
<223> OTHER INFORMATION: n = g, a, c or t

<400> SEQUENCE: 4
tgtttcaatt nagctcggtc ccggggatcc tctagagtcg acctnnaggc atgcaagctt      60
ggcactggcc gtcgttttac aacgtcgtga ctgggaaaac cctggcgtta cccaacttaa     120
tcgccttgca gcacatcccc ctttcgccag ctggcgtaat agcgaagagg cccgcaccga     180
tcgcccttcc caacagttgc gcagcctgaa tggcgaatgg cgcctgatgc ggtattttct     240
ccttacgcat ctgtgcggta tttcacaccg catatggtgc actctcagta caatctgctc     300
tgatgccgca tagttaagcc agccccgaca cccgccaaca cccgctgacg cgccctgacg     360
ggcttgtctg ctcccggcat ccgcttacag acaagctgtg accgtctccg ggagctgcat     420
gtgtcagagg ttttaccgta taccgaaacg cgcgaacgaa aggcctcgtg atcgcctatt     480
ttntaggtaa tgtatgatat atggttctta gacgtaggtg gcacttttcg ggaatgtgcg     540
cgaaccctat tgttattttt aancatcaaa tgatcgtatg aaaaaaccgt aat            593

<210> SEQ ID NO 5
<211> LENGTH: 555
<212> TYPE: DNA
<213> ORGANISM: Artificial Sequence
<220> FEATURE:
<223> OTHER INFORMATION: Description of Artificial Sequence:processed
      DNA sequencing data
<220> FEATURE:
<221> NAME/KEY: modified_base
<222> LOCATION: (1)..(555)
<223> OTHER INFORMATION: n = g, a, c or t

<400> SEQUENCE: 5
gntttnggta ccttagagac taagcttgat gcctgaggtc gactctagag gatccccggg      60
taccgagctc gaattcgccc tatagtgagt cgtattacaa ttcactggcc gtcgttttac     120
aacgtcgtga ctgggaaaac cctggcagtt acccaactta atcgccttgc agcacatccc     180
cctttcgcca gctggcgtaa tagcgaagag gcccgcaccg atcgcccttc ccaacagttg     240
cgcagcctga atggcgaatg gacgcgccct gtagcggcgc attaagcgcg gcgggtgtgg     300
tggttacgcg cagcgtgacc gctacacttg ccagcgccct agcgcccgct cctttcgctt     360
tcttcccttc ctttctcgcc acgttcgccg gctttccccg tcaagctcta aatcgggggc     420 tccctttaggg ttcgatttag tgcttacgga cctcgacccc aaaaacttga tagggtgatg     480
ggtacgtagt gggcatcgcc tgatgacggt tttcgccttt gacgttgagt cacgttttta     540
atagggactc tggtc                                                     555
```